US011600371B2

(12) United States Patent
Meschter et al.

(10) Patent No.: US 11,600,371 B2
(45) Date of Patent: *Mar. 7, 2023

(54) SYSTEMS AND METHODS FOR TIME-BASED ATHLETIC ACTIVITY MEASUREMENT AND DISPLAY

(71) Applicant: NIKE, Inc., Beaverton, OR (US)

(72) Inventors: James Meschter, Portland, OR (US); James Molyneux, Portland, OR (US); Aaron B. Weast, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/853,937

(22) Filed: Apr. 21, 2020

(65) Prior Publication Data
US 2020/0246662 A1 Aug. 6, 2020

Related U.S. Application Data

(60) Continuation of application No. 16/376,123, filed on Apr. 5, 2019, now Pat. No. 10,632,343, which is a
(Continued)

(51) Int. Cl.
G08B 23/00 (2006.01)
G16H 20/30 (2018.01)
(Continued)

(52) U.S. Cl.
CPC ......... *G16H 20/30* (2018.01); *A63B 24/0062* (2013.01); *G01B 5/02* (2013.01);
(Continued)

(58) Field of Classification Search
CPC ........ G16H 20/30; G16H 40/63; G16H 40/67; G16H 50/20; A63B 24/0062; G01B 5/02;
(Continued)

(56) References Cited

U.S. PATENT DOCUMENTS 3,270,564 A 9/1966 Evans
4,372,558 A 2/1983 Shimamoto et al.
(Continued)

FOREIGN PATENT DOCUMENTS

CA 2512601 A1 3/2002
CA 2668946 A1 5/2008
(Continued)

OTHER PUBLICATIONS

Aylward, "Sensemble : a wireless inertial sensor system for the interactive dance and collective motion analysis," Massachusetts Institute of Technology, School of Architecture and Planning, Program in Media Arts and Sciences, 2006, http://dspace.mitedu/handle/1721.1/37391 (3 pages).
(Continued)

*Primary Examiner* — Toan N Pham
(74) *Attorney, Agent, or Firm* — Banner & Witcoff, Ltd.

(57) ABSTRACT

An athletic parameter measurement device worn by an athlete during an athletic activity session includes a housing which attaches to the athlete, a display, a processor associated with the display, and an athletic parameter measurement sensor. During the athletic activity, the device detects, using the sensor, a vertical jump height of the athlete, and displays, during the performance of the athletic activity session, a representation of the vertical jump height on the display.

20 Claims, 26 Drawing Sheets

Related U.S. Application Data continuation of application No. 15/994,517, filed on May 31, 2018, now Pat. No. 10,293,209, which is a continuation of application No. 15/693,753, filed on Sep. 1, 2017, now Pat. No. 10,010,752, which is a division of application No. 15/223,188, filed on Jul. 29, 2016, now Pat. No. 9,757,619, which is a division of application No. 14/722,695, filed on May 27, 2015, now Pat. No. 9,429,411, which is a continuation of application No. 14/478,203, filed on Sep. 5, 2014, now Pat. No. 9,389,057, which is a continuation of application No. 13/293,653, filed on Nov. 10, 2011, now Pat. No. 8,831,407.

(60) Provisional application No. 61/412,285, filed on Nov. 10, 2010.

(51) Int. Cl.

| | | |
|---|---|---|
| *G16H 40/63* | (2018.01) | |
| *G16H 40/67* | (2018.01) | |
| *G16Z 99/00* | (2019.01) | |
| *H04N 5/92* | (2006.01) | |
| *H04N 7/18* | (2006.01) | |
| *A63B 24/00* | (2006.01) | |
| *G01B 5/02* | (2006.01) | |
| *G01P 15/09* | (2006.01) | |
| *G09B 5/02* | (2006.01) | |
| *G16H 50/20* | (2018.01) | |

(52) U.S. Cl.
CPC ............... *G01P 15/09* (2013.01); *G09B 5/02* (2013.01); *G16H 40/63* (2018.01); *G16H 40/67* (2018.01); *G16H 50/20* (2018.01); *G16Z 99/00* (2019.02); *H04N 5/9205* (2013.01); *H04N 7/181* (2013.01)

(58) Field of Classification Search
CPC .......... G01P 15/09; G09B 5/02; G16Z 99/00; H04N 5/9205; H04N 7/181
See application file for complete search history.

(56) References Cited

U.S. PATENT DOCUMENTS

| | | |
|---|---|---|
| 4,373,651 A | 2/1983 | Fanslow |
| 4,496,148 A | 1/1985 | Morstain et al. |
| 4,518,267 A | 5/1985 | Hepp |
| 4,578,969 A | 4/1986 | Larson |
| 4,647,918 A | 3/1987 | Goforth |
| 4,664,378 A | 5/1987 | Van Auken |
| 4,703,445 A | 10/1987 | Dassler |
| 4,745,930 A | 5/1988 | Confer |
| 4,814,661 A | 3/1989 | Ratzlaff et al. |
| 4,860,763 A | 8/1989 | Schminke |
| 4,866,412 A | 9/1989 | Rzepczynski |
| 4,890,111 A | 12/1989 | Nicolet et al. |
| 4,911,427 A | 3/1990 | Matsumoto et al. |
| 4,980,871 A | 12/1990 | Sieber et al. |
| 5,010,774 A | 4/1991 | Kikuo et al. |
| 5,033,291 A | 7/1991 | Podoloff et al. |
| 5,047,952 A | 9/1991 | Kramer et al. |
| 5,050,962 A | 9/1991 | Monnier et al. |
| 5,149,084 A | 9/1992 | Dalebout et al. |
| 5,150,536 A | 9/1992 | Strong |
| 5,154,960 A | 10/1992 | Mucci et al. |
| 5,249,967 A | 10/1993 | O'Leary et al. |
| 5,270,433 A | 12/1993 | Klauck et al. |
| 5,303,131 A | 4/1994 | Wu |
| 5,323,650 A | 6/1994 | Fullen et al. |
| 5,363,297 A | 11/1994 | Larson et al. |
| 5,373,651 A | 12/1994 | Wood |
| 5,374,821 A | 12/1994 | Muhs et al. |
| 5,393,651 A | 2/1995 | Hoshi |
| 5,408,873 A | 4/1995 | Schmidt et al. |
| 5,419,562 A | 5/1995 | Cromarty |
| 5,422,521 A | 6/1995 | Neer et al. |
| 5,444,462 A | 8/1995 | Wambach |
| 5,446,701 A | 8/1995 | Utke et al. |
| 5,471,405 A | 11/1995 | Marsh |
| 5,500,635 A | 3/1996 | Mott |
| 5,513,854 A | 5/1996 | Daver |
| 5,527,239 A | 6/1996 | Abbondanza |
| 5,626,538 A | 5/1997 | Dalebout et al. |
| 5,636,146 A | 6/1997 | Flentov et al. |
| 5,636,378 A | 6/1997 | Griffith |
| 5,638,300 A | 6/1997 | Johnson |
| 5,644,858 A | 7/1997 | Bemis |
| 5,655,316 A | 8/1997 | Huang |
| 5,694,514 A | 12/1997 | Evans et al. |
| 5,697,791 A | 12/1997 | Nashner et al. |
| 5,702,323 A | 12/1997 | Poulton |
| 5,714,706 A | 2/1998 | Nakada et al. |
| 5,720,200 A | 2/1998 | Anderson et al. |
| 5,724,265 A | 3/1998 | Hutchings |
| 5,764,786 A | 6/1998 | Kuwashima et al. |
| 5,785,666 A | 7/1998 | Costello et al. |
| 5,812,142 A | 9/1998 | Small et al. |
| 5,813,142 A | 9/1998 | Demon |
| 5,813,406 A | 9/1998 | Kramer et al. |
| 5,825,327 A | 10/1998 | Krasner |
| 5,844,861 A | 12/1998 | Maurer |
| 5,879,270 A | 3/1999 | Huish et al. |
| 5,888,172 A | 3/1999 | Andrus et al. |
| 5,889,464 A | 3/1999 | Huang |
| 5,903,454 A | 5/1999 | Hoffberg et al. |
| 5,907,819 A | 5/1999 | Johnson |
| 5,913,727 A | 6/1999 | Ahdoot |
| 5,929,332 A | 7/1999 | Brown |
| 5,960,380 A | 9/1999 | Flentov et al. |
| 5,963,891 A | 10/1999 | Walker et al. |
| 5,976,083 A | 11/1999 | Richardson et al. |
| 5,982,352 A | 11/1999 | Pryor |
| 6,002,982 A | 12/1999 | Fry |
| 6,013,007 A | 1/2000 | Root et al. |
| 6,017,128 A | 1/2000 | Goldston et al. |
| 6,018,705 A | 1/2000 | Gaudet et al. |
| 6,026,335 A | 2/2000 | Atlas |
| 6,042,492 A | 3/2000 | Baum |
| 6,050,962 A | 4/2000 | Kramer et al. |
| 6,066,075 A | 5/2000 | Poulton |
| 6,073,086 A | 6/2000 | Marinelli |
| 6,077,193 A | 6/2000 | Buhler et al. |
| 6,081,750 A | 6/2000 | Hoffberg et al. |
| 6,122,340 A | 9/2000 | Darley et al. |
| 6,122,846 A | 9/2000 | Gray et al. |
| 6,141,041 A | 10/2000 | Carlbom et al. |
| 6,148,262 A | 11/2000 | Fry |
| 6,148,271 A | 11/2000 | Marinelli |
| 6,148,280 A | 11/2000 | Kramer |
| 6,151,563 A | 11/2000 | Marinelli |
| 6,157,898 A | 12/2000 | Marinelli |
| 6,174,294 B1 | 1/2001 | Crabb et al. |
| 6,195,921 B1 | 3/2001 | Truong |
| 6,198,394 B1 | 3/2001 | Jacobsen et al. |
| 6,204,813 B1 | 3/2001 | Wadell et al. |
| 6,226,577 B1 | 5/2001 | Yeo |
| 6,266,623 B1 | 7/2001 | Vock et al. |
| 6,270,433 B1 | 8/2001 | Orenstein et al. |
| 6,287,200 B1 | 9/2001 | Sharma |
| 6,298,314 B1 | 10/2001 | Blackadar et al. |
| 6,308,565 B1 | 10/2001 | French et al. |
| 6,320,173 B1 | 11/2001 | Vock et al. |
| 6,330,757 B1 | 12/2001 | Russell |
| 6,336,365 B1 | 1/2002 | Blackadar et al. |
| 6,336,891 B1 | 1/2002 | Fedrigon et al. |
| 6,356,856 B1 | 3/2002 | Damen et al. |
| 6,357,147 B1 | 3/2002 | Darley et al. |
| 6,360,597 B1 | 3/2002 | Hubbard, Jr. |
| 6,418,181 B1 | 7/2002 | Nissila |
| 6,426,490 B1 | 7/2002 | Storz |
| 6,428,490 B1 | 8/2002 | Kramer et al. |

(56) References Cited

U.S. PATENT DOCUMENTS

| | | |
|---|---|---|
| 6,430,843 B1 | 8/2002 | Potter et al. |
| 6,443,904 B2 | 9/2002 | Nissila |
| 6,458,060 B1 | 10/2002 | Watterson et al. |
| 6,496,787 B1 | 12/2002 | Flentov et al. |
| 6,496,952 B1 | 12/2002 | Osada et al. |
| 6,498,994 B2 | 12/2002 | Vock et al. |
| 6,515,284 B1 | 2/2003 | Walle et al. |
| 6,516,284 B2 | 2/2003 | Flentov et al. |
| 6,527,674 B1 | 3/2003 | Clem |
| 6,536,139 B2 | 3/2003 | Darley et al. |
| 6,539,336 B1 | 3/2003 | Vock et al. |
| 6,544,858 B1 | 4/2003 | Beekman et al. |
| 6,560,903 B1 | 5/2003 | Darley |
| 6,567,038 B1 | 5/2003 | Granot et al. |
| 6,567,116 B1 | 5/2003 | Aman et al. |
| 6,578,291 B2 | 6/2003 | Hirsch et al. |
| 6,582,330 B1 | 6/2003 | Rehkemper et al. |
| 6,585,622 B1 | 7/2003 | Shum et al. |
| 6,601,016 B1 | 7/2003 | Brown et al. |
| 6,607,493 B2 | 8/2003 | Song |
| 6,611,789 B1 | 8/2003 | Darley |
| 6,620,057 B1 | 9/2003 | Pirritano et al. |
| 6,640,144 B1 | 10/2003 | Huang et al. |
| 6,648,798 B2 | 11/2003 | Yoo |
| 6,656,042 B2 | 12/2003 | Reiss et al. |
| 6,656,091 B1 | 12/2003 | Abelbeck et al. |
| 6,671,390 B1 | 12/2003 | Barbour et al. |
| 6,672,991 B2 | 1/2004 | O'Malley |
| 6,687,535 B2 | 2/2004 | Hautala et al. |
| 6,707,487 B1 | 3/2004 | Aman et al. |
| 6,710,713 B1 | 3/2004 | Russo |
| 6,718,200 B2 | 4/2004 | Marmaropoulos et al. |
| 6,736,759 B1 | 5/2004 | Stubbs et al. |
| 6,748,462 B2 | 6/2004 | Dubil et al. |
| 6,778,973 B2 | 8/2004 | Harlan |
| 6,784,826 B2 | 8/2004 | Kane et al. |
| 6,785,579 B2 | 8/2004 | Huang et al. |
| 6,785,805 B1 | 8/2004 | House et al. |
| 6,786,848 B2 | 9/2004 | Yamashita et al. |
| 6,796,927 B2 | 9/2004 | Toyama |
| 6,808,462 B2 | 10/2004 | Snyder et al. |
| 6,829,512 B2 | 12/2004 | Huang et al. |
| 6,831,603 B2 | 12/2004 | Menache |
| 6,836,744 B1 | 12/2004 | Asphahani et al. |
| 6,858,006 B2 | 2/2005 | MacCarter et al. |
| 6,876,947 B1 | 4/2005 | Darley et al. |
| 6,882,897 B1 | 4/2005 | Fernandez |
| 6,885,971 B2 | 4/2005 | Vock et al. |
| 6,889,282 B2 | 5/2005 | Schollenberger |
| 6,892,216 B2 | 5/2005 | Coburn, II et al. |
| 6,902,513 B1 | 6/2005 | McClure |
| 6,909,420 B1 | 6/2005 | Nicolas et al. |
| 6,922,664 B1 | 7/2005 | Fernandez et al. |
| 6,932,698 B2 | 8/2005 | Sprogis |
| 6,959,259 B2 | 10/2005 | Vock et al. |
| 6,963,818 B2 | 11/2005 | Flentov et al. |
| 6,978,320 B2 | 12/2005 | Nonaka |
| 6,997,852 B2 | 2/2006 | Watterson et al. |
| 6,997,882 B2 | 2/2006 | Parker et al. |
| 7,005,970 B2 | 2/2006 | Hodsdon et al. |
| 7,030,861 B1 | 4/2006 | Westerman et al. |
| 7,040,998 B2 | 5/2006 | Jolliffe et al. |
| 7,045,151 B2 | 5/2006 | Trant |
| 7,046,151 B2 | 5/2006 | Dundon |
| 7,054,678 B2 | 5/2006 | Dardik et al. |
| 7,054,784 B2 | 5/2006 | Flentov et al. |
| 7,057,551 B1 | 6/2006 | Vogt |
| 7,070,571 B2 | 7/2006 | Kramer et al. |
| 7,072,789 B2 | 7/2006 | Vock et al. |
| 7,076,291 B2 | 7/2006 | Pulkkinen et al. |
| 7,091,863 B2 | 8/2006 | Ravet |
| 7,092,846 B2 | 8/2006 | Vock et al. |
| 7,097,588 B2 | 8/2006 | Watterson et al. |
| 7,139,582 B2 | 11/2006 | Couronne et al. |
| 7,152,343 B2 | 12/2006 | Whatley |
| 7,162,392 B2 | 1/2007 | Vock et al. |
| 7,166,062 B1 | 1/2007 | Watterson et al. |
| 7,171,331 B2 | 1/2007 | Vock et al. |
| 7,174,277 B2 | 2/2007 | Vock et al. |
| 7,200,517 B2 | 4/2007 | Darley et al. |
| 7,245,898 B2 | 7/2007 | Van Bosch et al. |
| 7,273,431 B2 | 9/2007 | DeVall |
| 7,277,021 B2 | 10/2007 | Beebe |
| 7,283,647 B2 | 10/2007 | McNitt |
| 7,304,580 B2 | 12/2007 | Sullivan et al. |
| 7,310,895 B2 | 12/2007 | Whittlesey et al. |
| 7,321,330 B2 | 1/2008 | Sajima |
| 7,383,728 B2 | 6/2008 | Noble et al. |
| 7,391,886 B1 | 6/2008 | Clark et al. |
| RE40,474 E | 9/2008 | Quellais et al. |
| 7,426,873 B1 | 9/2008 | Kholwadwala et al. |
| 7,428,471 B2 | 9/2008 | Darley et al. |
| 7,433,805 B2 | 10/2008 | Vock et al. |
| 7,457,724 B2 | 11/2008 | Vock et al. |
| 7,480,512 B2 | 1/2009 | Graham et al. |
| 7,487,045 B1 | 2/2009 | Vieira |
| 7,497,037 B2 | 3/2009 | Vick et al. |
| 7,498,856 B2 | 3/2009 | Lin et al. |
| 7,498,956 B2 | 3/2009 | Baier et al. |
| 7,513,852 B2 | 4/2009 | Wilkins et al. |
| 7,522,970 B2 | 4/2009 | Fernandez |
| 7,552,549 B2 | 6/2009 | Whittlesey et al. |
| 7,556,589 B1 | 7/2009 | Stearns et al. |
| 7,559,877 B2 | 7/2009 | Parks et al. |
| 7,579,946 B2 | 8/2009 | Case, Jr. |
| 7,596,891 B2 | 10/2009 | Carnes et al. |
| 7,602,301 B1 | 10/2009 | Stirling et al. |
| 7,607,243 B2 | 10/2009 | Berner, Jr. et al. |
| 7,617,068 B2 | 11/2009 | Tadin et al. |
| 7,620,466 B2 | 11/2009 | Neale et al. |
| 7,623,987 B2 | 11/2009 | Vock et al. |
| 7,625,314 B2 | 12/2009 | Ungari et al. |
| 7,627,451 B2 | 12/2009 | Vock et al. |
| 7,634,379 B2 | 12/2009 | Noble |
| 7,641,592 B2 | 1/2010 | Roche |
| 7,651,442 B2 | 1/2010 | Carlson |
| 7,658,694 B2 | 2/2010 | Ungari |
| 7,670,263 B2 | 3/2010 | Ellis et al. |
| 7,698,830 B2 | 4/2010 | Townsend et al. |
| 7,699,753 B2 | 4/2010 | Daikeler et al. |
| 7,722,502 B2 | 5/2010 | Holkkola |
| 7,726,206 B2 | 6/2010 | Terrafranca, Jr. et al. |
| 7,739,076 B1 | 6/2010 | Vock et al. |
| 7,758,523 B2 | 7/2010 | Collings et al. |
| 7,771,320 B2 | 8/2010 | Riley et al. |
| 7,791,808 B2 | 9/2010 | French et al. |
| 7,805,150 B2 | 9/2010 | Graham et al. |
| 7,810,392 B2 | 10/2010 | Kitagawa |
| 7,816,632 B2 | 10/2010 | Bourke, III et al. |
| 7,840,378 B2 | 11/2010 | Vock et al. |
| 7,850,514 B2 | 12/2010 | Weber |
| 7,901,325 B2 | 3/2011 | Henderson |
| 7,905,815 B2 | 3/2011 | Ellis et al. |
| 7,909,737 B2 | 3/2011 | Ellis et al. |
| 7,921,716 B2 | 4/2011 | Morris Bamberg et al. |
| 7,927,253 B2 | 4/2011 | Vincent et al. |
| 7,934,983 B1 | 5/2011 | Eisner |
| 7,997,007 B2 | 8/2011 | Sanabria-Hernandez |
| 8,002,645 B2 | 8/2011 | Savarese et al. |
| 8,054,176 B2 | 11/2011 | Karjalainen |
| 8,056,268 B2 | 11/2011 | DiBenedetto et al. |
| 8,061,061 B1 | 11/2011 | Rivas |
| 8,066,514 B2 | 11/2011 | Clarke |
| 8,070,620 B2 | 12/2011 | Rankin |
| 8,083,643 B2 | 12/2011 | Ng et al. |
| 8,099,258 B2 | 1/2012 | Alten et al. |
| 8,109,858 B2 | 2/2012 | Redmann |
| 8,131,498 B1 | 3/2012 | McCauley |
| 8,142,267 B2 | 3/2012 | Adams |
| 8,172,722 B2 | 5/2012 | Molyneux et al. |
| 8,177,260 B2 | 5/2012 | Tropper et al. |
| 8,212,136 B2 | 7/2012 | Shirai et al. |
| 8,212,158 B2 | 7/2012 | Wiest |
| 8,221,290 B2 | 7/2012 | Vincent et al. |

(56) References Cited

U.S. PATENT DOCUMENTS

| | | |
|---|---|---|
| 8,251,930 B2 | 8/2012 | Ido |
| 8,253,586 B1 | 8/2012 | Matak |
| 8,257,189 B2 | 9/2012 | Koudele et al. |
| 8,291,618 B2 | 10/2012 | Ellis |
| 8,333,643 B2 | 12/2012 | Eisner |
| 8,337,212 B2 | 12/2012 | Prstojevich |
| 8,346,524 B2 | 1/2013 | Turgiss et al. |
| 8,353,791 B2 | 1/2013 | Holthouse et al. |
| 8,360,904 B2 | 1/2013 | Oleson et al. |
| 8,467,979 B2 | 6/2013 | Sobolewski |
| 8,474,153 B2 | 7/2013 | Brie et al. |
| 8,484,654 B2 | 7/2013 | Graham et al. |
| 8,568,277 B2 | 10/2013 | Johnson |
| 8,676,541 B2 | 3/2014 | Schrock et al. |
| 8,739,639 B2 | 6/2014 | Owings et al. |
| 8,784,274 B1 | 7/2014 | Chuang |
| 8,814,755 B2 | 8/2014 | Ellis et al. |
| 8,831,407 B2 | 9/2014 | Meschter et al. |
| 8,845,496 B2 | 9/2014 | Arrasvuori et al. |
| 8,860,584 B1 | 10/2014 | Matak |
| 9,389,057 B2 | 7/2016 | Meschter et al. |
| 9,390,229 B1 | 7/2016 | Kahn et al. |
| 9,429,411 B2 | 8/2016 | Meschter et al. |
| 9,504,414 B2 | 11/2016 | Coza et al. |
| 9,757,619 B2 | 9/2017 | Meschter et al. |
| 10,610,761 B1 | 4/2020 | Matak et al. |
| 2001/0054043 A1 | 12/2001 | Harlan |
| 2002/0035184 A1 | 3/2002 | Plaver et al. |
| 2002/0077219 A1 | 6/2002 | Cohen et al. |
| 2002/0134153 A1 | 9/2002 | Grenlund |
| 2002/0160883 A1 | 10/2002 | Dugan |
| 2002/0170193 A1 | 11/2002 | Townsend et al. |
| 2003/0009308 A1 | 1/2003 | Kirtley |
| 2003/0049590 A1 | 3/2003 | Feldbau |
| 2003/0054327 A1 | 3/2003 | Evensen |
| 2003/0065561 A1 | 4/2003 | Brown et al. |
| 2003/0097878 A1 | 5/2003 | Farringdon et al. |
| 2003/0134714 A1 | 7/2003 | Oishi et al. |
| 2003/0148762 A1 | 8/2003 | Noe |
| 2003/0163287 A1 | 8/2003 | Vock et al. |
| 2003/0190062 A1 | 10/2003 | Noro et al. |
| 2003/0207718 A1 | 11/2003 | Perlmutter |
| 2004/0006680 A1 | 1/2004 | Duncan |
| 2004/0125013 A1 | 7/2004 | Haselsteiner et al. |
| 2004/0154190 A1 | 8/2004 | Munster |
| 2004/0215413 A1 | 10/2004 | Weldum et al. |
| 2004/0218317 A1 | 11/2004 | Kawazu et al. |
| 2004/0226192 A1 | 11/2004 | Geer et al. |
| 2005/0011085 A1 | 1/2005 | Swigart et al. |
| 2005/0032582 A1 | 2/2005 | Mahajan et al. |
| 2005/0038679 A1 | 2/2005 | Short |
| 2005/0046576 A1 | 3/2005 | Julian et al. |
| 2005/0070809 A1 | 3/2005 | Acres |
| 2005/0106977 A1 | 5/2005 | Coulston |
| 2005/0143199 A1 | 6/2005 | Saroyan |
| 2005/0162257 A1 | 7/2005 | Gonzalez |
| 2005/0176373 A1 | 8/2005 | Gilbert et al. |
| 2005/0183292 A1 | 8/2005 | DiBenedetto et al. |
| 2005/0187644 A1 | 8/2005 | Neale et al. |
| 2005/0188566 A1 | 9/2005 | Whittlesey et al. |
| 2005/0221403 A1 | 10/2005 | Gazenko |
| 2005/0234307 A1 | 10/2005 | Heinonen et al. |
| 2005/0250458 A1 | 11/2005 | Graham et al. |
| 2005/0261609 A1 | 11/2005 | Collings et al. |
| 2005/0270156 A1 | 12/2005 | Ravet |
| 2005/0272564 A1 | 12/2005 | Pyles et al. |
| 2005/0282633 A1 | 12/2005 | Nicolas et al. |
| 2006/0003872 A1 | 1/2006 | Chiles et al. |
| 2006/0010174 A1 | 1/2006 | Nguyen et al. |
| 2006/0017692 A1 | 1/2006 | Wehrenberg et al. |
| 2006/0025229 A1 | 2/2006 | Mahajan et al. |
| 2006/0025282 A1 | 2/2006 | Redmann |
| 2006/0026120 A1 | 2/2006 | Carolan et al. |
| 2006/0040244 A1 | 2/2006 | Kain |
| 2006/0084850 A1 | 4/2006 | Spinner et al. |
| 2006/0091715 A1 | 5/2006 | Schmitz et al. |
| 2006/0111944 A1 | 5/2006 | Sirmans et al. |
| 2006/0136173 A1 | 6/2006 | Case et al. |
| 2006/0143645 A1 | 6/2006 | Vock et al. |
| 2006/0144152 A1 | 7/2006 | Cabuz et al. |
| 2006/0148594 A1 | 7/2006 | Saintoyant et al. |
| 2006/0178235 A1 | 8/2006 | Coughlan et al. |
| 2006/0189440 A1 | 8/2006 | Gravagne |
| 2006/0205569 A1 | 9/2006 | Watterson et al. |
| 2006/0217231 A1 | 9/2006 | Parks et al. |
| 2006/0226843 A1 | 10/2006 | Al-Anbuky et al. |
| 2006/0248749 A1 | 11/2006 | Ellis |
| 2006/0262120 A1 | 11/2006 | Rosenberg |
| 2007/0006489 A1 | 1/2007 | Case et al. |
| 2007/0016091 A1 | 1/2007 | Butt et al. |
| 2007/0021269 A1 | 1/2007 | Shum |
| 2007/0026421 A1 | 2/2007 | Sundberg et al. |
| 2007/0032345 A1 | 2/2007 | Padmanabhan et al. |
| 2007/0032748 A1 | 2/2007 | McNeil et al. |
| 2007/0033838 A1 | 2/2007 | Luce et al. |
| 2007/0059675 A1 | 3/2007 | Kuenzler et al. |
| 2007/0060408 A1 | 3/2007 | Schultz et al. |
| 2007/0060425 A1 | 3/2007 | Kuenzler et al. |
| 2007/0063849 A1 | 3/2007 | Rosella et al. |
| 2007/0063850 A1 | 3/2007 | Devaul et al. |
| 2007/0067885 A1 | 3/2007 | Fernandez |
| 2007/0068244 A1 | 3/2007 | Billing et al. |
| 2007/0069014 A1 | 3/2007 | Heckel et al. |
| 2007/0073178 A1 | 3/2007 | Browning et al. |
| 2007/0078324 A1 | 4/2007 | Wijisiriwardana |
| 2007/0082389 A1 | 4/2007 | Clark et al. |
| 2007/0094890 A1 | 5/2007 | Cho et al. |
| 2007/0105629 A1 | 5/2007 | Toyama |
| 2007/0118328 A1 | 5/2007 | Vock et al. |
| 2007/0135225 A1 | 6/2007 | Nieminen et al. |
| 2007/0135243 A1 | 6/2007 | LaRue et al. |
| 2007/0143452 A1 | 6/2007 | Suenbuel et al. |
| 2007/0149361 A1 | 6/2007 | Jung et al. |
| 2007/0152812 A1 | 7/2007 | Wong et al. |
| 2007/0156335 A1 | 7/2007 | McBride et al. |
| 2007/0173705 A1 | 7/2007 | Teller et al. |
| 2007/0178967 A1 | 8/2007 | Rosenberg |
| 2007/0179977 A1 | 8/2007 | Reed et al. |
| 2007/0187266 A1 | 8/2007 | Porter et al. |
| 2007/0191083 A1 | 8/2007 | Kuenzler et al. |
| 2007/0207447 A1 | 9/2007 | Lamar et al. |
| 2007/0208544 A1 | 9/2007 | Kulach et al. |
| 2007/0232455 A1 | 10/2007 | Hanoun |
| 2007/0239479 A1 | 10/2007 | Arrasvuori et al. |
| 2007/0250286 A1 | 10/2007 | Duncan et al. |
| 2007/0260421 A1 | 11/2007 | Berner et al. |
| 2007/0283599 A1 | 12/2007 | Talbott |
| 2007/0299625 A1 | 12/2007 | Englert et al. |
| 2008/0009068 A1 | 1/2008 | Georges |
| 2008/0027679 A1 | 1/2008 | Shklarski |
| 2008/0028783 A1 | 2/2008 | Immel et al. |
| 2008/0031492 A1 | 2/2008 | Lanz |
| 2008/0039203 A1 | 2/2008 | Ackley et al. |
| 2008/0048616 A1 | 2/2008 | Paul et al. |
| 2008/0056508 A1 | 3/2008 | Pierce et al. |
| 2008/0060224 A1 | 3/2008 | Whittlesey et al. |
| 2008/0061023 A1 | 3/2008 | Moor |
| 2008/0066343 A1 | 3/2008 | Sanabria-Hernandez |
| 2008/0066560 A1 | 3/2008 | Yu et al. |
| 2008/0080626 A1 | 4/2008 | Lawrence et al. |
| 2008/0084351 A1 | 4/2008 | Englert et al. |
| 2008/0085790 A1 | 4/2008 | Englert |
| 2008/0088303 A1 | 4/2008 | Englert |
| 2008/0090683 A1 | 4/2008 | Englert et al. |
| 2008/0090685 A1 | 4/2008 | Namie et al. |
| 2008/0104247 A1 | 5/2008 | Venkatakrishnan et al. |
| 2008/0109158 A1 | 5/2008 | Huhtala et al. |
| 2008/0119479 A1 | 5/2008 | Wedge |
| 2008/0127527 A1 | 6/2008 | Chen |
| 2008/0134583 A1 | 6/2008 | Polus |
| 2008/0146302 A1 | 6/2008 | Olsen et al. |
| 2008/0165140 A1 | 7/2008 | Christie et al. |
| 2008/0172498 A1 | 7/2008 | Boucard |
| 2008/0177507 A1 | 7/2008 | Mian et al. |

(56) References Cited

U.S. PATENT DOCUMENTS

| | | |
|---|---|---|
| 2008/0188353 A1 | 8/2008 | Vitolo et al. |
| 2008/0200312 A1 | 8/2008 | Tagliabue |
| 2008/0203144 A1 | 8/2008 | Kim |
| 2008/0207401 A1 | 8/2008 | Harding et al. |
| 2008/0218310 A1 | 9/2008 | Alten et al. |
| 2008/0221403 A1 | 9/2008 | Fernandez |
| 2008/0246629 A1 | 10/2008 | Tsui et al. |
| 2008/0249736 A1 | 10/2008 | Prstojevich |
| 2008/0255794 A1 | 10/2008 | Levine |
| 2008/0258921 A1 | 10/2008 | Woo et al. |
| 2008/0259028 A1 | 10/2008 | Teepell et al. |
| 2008/0261776 A1 | 10/2008 | Skiba |
| 2008/0269644 A1 | 10/2008 | Ray |
| 2008/0274755 A1 | 11/2008 | Cholkar et al. |
| 2008/0284650 A1 | 11/2008 | MacIntosh et al. |
| 2008/0286733 A1 | 11/2008 | Claudel et al. |
| 2008/0287832 A1 | 11/2008 | Collins et al. |
| 2008/0288200 A1 | 11/2008 | Noble |
| 2008/0293023 A1 | 11/2008 | Diehl et al. |
| 2008/0297832 A1 | 12/2008 | Otsuka |
| 2008/0300914 A1 | 12/2008 | Karkanias et al. |
| 2008/0306410 A1 | 12/2008 | Kalpaxis et al. |
| 2008/0307899 A1 | 12/2008 | Von Lilienfeld-Toal et al. |
| 2008/0316325 A1 | 12/2008 | Nakahara |
| 2008/0318679 A1 | 12/2008 | Tran et al. |
| 2009/0018691 A1 | 1/2009 | Fernandez |
| 2009/0027917 A1 | 1/2009 | Chen et al. |
| 2009/0048039 A1 | 2/2009 | Holthouse et al. |
| 2009/0048044 A1 | 2/2009 | Oleson et al. |
| 2009/0048070 A1 | 2/2009 | Vincent et al. |
| 2009/0048538 A1 | 2/2009 | Levine et al. |
| 2009/0048918 A1 | 2/2009 | Dawson et al. |
| 2009/0050699 A1 | 2/2009 | Basar et al. |
| 2009/0061837 A1 | 3/2009 | Chaudhri et al. |
| 2009/0069156 A1 | 3/2009 | Kurunmaki et al. |
| 2009/0075347 A1 | 3/2009 | Cervin et al. |
| 2009/0076341 A1 | 3/2009 | James et al. |
| 2009/0090683 A1 | 4/2009 | Haghayegh |
| 2009/0105047 A1 | 4/2009 | Guidi et al. |
| 2009/0107009 A1 | 4/2009 | Bishop et al. |
| 2009/0135001 A1 | 5/2009 | Yuk |
| 2009/0137933 A1 | 5/2009 | Lieberman et al. |
| 2009/0144084 A1 | 6/2009 | Neumaier |
| 2009/0144369 A1 | 6/2009 | Brown |
| 2009/0149299 A1 | 6/2009 | Tchao |
| 2009/0150178 A1 | 6/2009 | Sutton et al. |
| 2009/0152456 A1 | 6/2009 | Waid et al. |
| 2009/0153369 A1 | 6/2009 | Baier et al. |
| 2009/0153477 A1 | 6/2009 | Saenz |
| 2009/0163287 A1 | 6/2009 | Vald'Via et al. |
| 2009/0167677 A1 | 7/2009 | Kruse et al. |
| 2009/0171614 A1 | 7/2009 | Damen |
| 2009/0189982 A1 | 7/2009 | Tawiah |
| 2009/0210078 A1 | 8/2009 | Crowley |
| 2009/0233770 A1 | 9/2009 | Vincent et al. |
| 2009/0235739 A1 | 9/2009 | Morris Bamberg et al. |
| 2009/0258710 A1 | 10/2009 | Quatrochi et al. |
| 2009/0259566 A1 | 10/2009 | White, III et al. |
| 2009/0262088 A1 | 10/2009 | Moll-Carrillo et al. |
| 2009/0293319 A1 | 12/2009 | Avni |
| 2009/0297832 A1 | 12/2009 | Hatta et al. |
| 2010/0000121 A1 | 1/2010 | Brodie et al. |
| 2010/0004566 A1 | 1/2010 | Son et al. |
| 2010/0023231 A1 | 1/2010 | Allgaier et al. |
| 2010/0023531 A1 | 1/2010 | Brisebois et al. |
| 2010/0035688 A1 | 2/2010 | Picunko |
| 2010/0053867 A1 | 3/2010 | Ellis et al. |
| 2010/0056340 A1 | 3/2010 | Ellis et al. |
| 2010/0057951 A1 | 3/2010 | Ellis et al. |
| 2010/0059561 A1 | 3/2010 | Ellis et al. |
| 2010/0062740 A1 | 3/2010 | Ellis et al. |
| 2010/0063778 A1 | 3/2010 | Schrock et al. |
| 2010/0063779 A1 | 3/2010 | Schrock et al. |
| 2010/0065836 A1 | 3/2010 | Lee |
| 2010/0072948 A1 | 3/2010 | Sun et al. |
| 2010/0082735 A1 | 4/2010 | Petersen et al. |
| 2010/0088023 A1 | 4/2010 | Werner |
| 2010/0094147 A1 | 4/2010 | Inan et al. |
| 2010/0111705 A1 | 5/2010 | Sato et al. |
| 2010/0113160 A1 | 5/2010 | Belz et al. |
| 2010/0125028 A1 | 5/2010 | Heppert |
| 2010/0129780 A1 | 5/2010 | Homsi et al. |
| 2010/0152619 A1 | 6/2010 | Kalpaxis et al. |
| 2010/0184563 A1 | 7/2010 | Molyneux et al. |
| 2010/0184564 A1 | 7/2010 | Molyneux et al. |
| 2010/0191490 A1 | 7/2010 | Martens et al. |
| 2010/0201500 A1 | 8/2010 | Stirling et al. |
| 2010/0201512 A1 | 8/2010 | Stirling et al. |
| 2010/0204616 A1 | 8/2010 | Shears et al. |
| 2010/0225763 A1 | 9/2010 | Vock et al. |
| 2010/0231580 A1 | 9/2010 | Miyasaka |
| 2010/0273610 A1 | 10/2010 | Johnson |
| 2010/0277617 A1 | 11/2010 | Hollinger |
| 2010/0279822 A1 | 11/2010 | Ford |
| 2010/0286601 A1 | 11/2010 | Yodat et al. |
| 2010/0292599 A1 | 11/2010 | Oleson et al. |
| 2010/0298659 A1 | 11/2010 | McCombie et al. |
| 2010/0312083 A1 | 12/2010 | Southerland |
| 2010/0332188 A1 | 12/2010 | Vock et al. |
| 2011/0003665 A1 | 1/2011 | Burton et al. |
| 2011/0021280 A1 | 1/2011 | Boroda et al. |
| 2011/0087445 A1 | 4/2011 | Sobolewski |
| 2011/0107369 A1 | 5/2011 | O'Brien et al. |
| 2011/0119027 A1 | 5/2011 | Zhu et al. |
| 2011/0119058 A1 | 5/2011 | Berard et al. |
| 2011/0136627 A1 | 6/2011 | Williams |
| 2011/0152695 A1 | 6/2011 | Granqvist et al. |
| 2011/0208444 A1 | 8/2011 | Solinsky |
| 2011/0230986 A1 | 9/2011 | Lafortune et al. |
| 2011/0305369 A1* | 12/2011 | Bentley .................. G06V 40/23 340/572.1 |
| 2012/0041767 A1 | 2/2012 | Hoffman et al. |
| 2012/0050351 A1 | 3/2012 | Dobler et al. |
| 2012/0050529 A1 | 3/2012 | Bentley |
| 2012/0203360 A1 | 8/2012 | Tagliabue |
| 2012/0234111 A1 | 9/2012 | Molyneux et al. |
| 2012/0277040 A1 | 11/2012 | Vincent et al. |
| 2012/0291563 A1 | 11/2012 | Schrock et al. |
| 2012/0291564 A1 | 11/2012 | Amos et al. |
| 2013/0079907 A1 | 3/2013 | Homsi et al. |
| 2013/0213145 A1 | 8/2013 | Owings et al. |
| 2014/0033572 A1 | 2/2014 | Steier et al. |
| 2014/0174205 A1 | 6/2014 | Clarke et al. |
| 2014/0228986 A1 | 8/2014 | Case, Jr. et al. |
| 2014/0342329 A1 | 11/2014 | Debenedetto et al. |
| 2015/0062440 A1 | 3/2015 | Baxter et al. |
| 2016/0332029 A1 | 11/2016 | Meschter et al. |
| 2017/0004358 A1* | 1/2017 | Bose ..................... G06F 3/038 |

FOREIGN PATENT DOCUMENTS

| | | |
|---|---|---|
| CN | 1101757 A | 4/1995 |
| CN | 1231753 A | 10/1999 |
| CN | 1839724 A | 10/2006 |
| CN | 200977748 Y | 11/2007 |
| CN | 200994779 Y | 12/2007 |
| CN | 101240461 A | 8/2008 |
| CN | 101242880 A | 8/2008 |
| CN | 101367011 A | 2/2009 |
| CN | 101367012 A | 2/2009 |
| CN | 201409198 Y | 2/2010 |
| CN | 101784230 A | 7/2010 |
| CN | 101890215 A | 11/2010 |
| CN | 101894206 A | 11/2010 |
| CN | 102143695 A | 8/2011 |
| CN | 201948063 U | 8/2011 |
| DE | 202004006680 U1 | 3/2005 |
| EP | 0160880 A1 | 11/1985 |
| EP | 0662600 A1 | 7/1995 |
| EP | 0956819 A1 | 11/1999 |
| EP | 1042686 A2 | 10/2000 |
| EP | 1707065 A1 | 10/2006 |
| EP | 2025370 A1 | 2/2009 |
| EP | 2025372 A2 | 2/2009 |

(56) References Cited

FOREIGN PATENT DOCUMENTS

| | | |
|---|---|---|
| EP | 2189191 A2 | 5/2010 |
| EP | 2324762 A1 | 5/2011 |
| EP | 2363179 A2 | 9/2011 |
| FR | 2929827 A1 | 10/2009 |
| GB | 251054 A | 4/1926 |
| GB | 2246891 A | 2/1992 |
| GB | 2421416 A | 6/2006 |
| JP | S62044275 A | 2/1987 |
| JP | S62055580 A | 3/1987 |
| JP | H0355077 A | 3/1991 |
| JP | 0561724 | 6/1993 |
| JP | H07056990 A | 3/1995 |
| JP | H0938051 A | 2/1997 |
| JP | H10090396 | 4/1998 |
| JP | H11248724 A | 9/1999 |
| JP | H11339009 A | 12/1999 |
| JP | 2002163404 A | 6/2002 |
| JP | 2003078864 A | 3/2003 |
| JP | 2003141260 A | 5/2003 |
| JP | 2003264503 A | 9/2003 |
| JP | 2004024627 A | 1/2004 |
| JP | 2004304653 A | 10/2004 |
| JP | 2005073094 A | 3/2005 |
| JP | 2005156531 A | 6/2005 |
| JP | 2005269086 A | 9/2005 |
| JP | 2005270640 A | 10/2005 |
| JP | 2006031504 A | 2/2006 |
| JP | 2006034717 A | 2/2006 |
| JP | 2006209468 A | 8/2006 |
| JP | 2006518247 A | 8/2006 |
| JP | 2006302122 A | 11/2006 |
| JP | 2006319876 A | 11/2006 |
| JP | 2007134473 A | 5/2007 |
| JP | 200715117 | 6/2007 |
| JP | 2008061193 A | 3/2008 |
| JP | 2008073209 A | 4/2008 |
| JP | 2008524589 | 7/2008 |
| JP | 2009045452 A | 3/2009 |
| JP | 2009045462 A | 3/2009 |
| JP | 2009073610 A | 4/2009 |
| JP | 2009148338 A | 7/2009 |
| JP | 2010085530 A | 4/2010 |
| JP | 2010088886 A | 4/2010 |
| JP | 2010114547 A | 5/2010 |
| JP | 2010166322 A | 7/2010 |
| JP | 2010236951 A | 10/2010 |
| WO | 98007341 A2 | 2/1998 |
| WO | 200033031 A1 | 6/2000 |
| WO | 2001045014 A1 | 6/2001 |
| WO | 0166201 A1 | 9/2001 |
| WO | 2002035184 A2 | 5/2002 |
| WO | 2002035997 A1 | 5/2002 |
| WO | 2002055959 A1 | 7/2002 |
| WO | 2002067449 A2 | 8/2002 |
| WO | 2002101408 A1 | 12/2002 |
| WO | 2004066837 A1 | 8/2004 |
| WO | 2004067109 A2 | 8/2004 |
| WO | 2005050868 A1 | 6/2005 |
| WO | 2006065679 | 6/2006 |
| WO | 2006091715 A1 | 8/2006 |
| WO | 2006111687 A1 | 10/2006 |
| WO | 2007064735 A2 | 6/2007 |
| WO | 2007069014 A1 | 6/2007 |
| WO | 2007082389 A1 | 7/2007 |
| WO | 2008033338 A2 | 3/2008 |
| WO | 2008060043 A1 | 5/2008 |
| WO | 2008061023 A2 | 5/2008 |
| WO | 2008080626 A1 | 7/2008 |
| WO | 2008010085 | 8/2008 |
| WO | 2008101085 A2 | 8/2008 |
| WO | 2008104247 A1 | 9/2008 |
| WO | 2008119479 A1 | 10/2008 |
| WO | 2008134583 A1 | 11/2008 |
| WO | 2009027917 A1 | 3/2009 |
| WO | 2009073610 A2 | 6/2009 |
| WO | 2009126818 A2 | 10/2009 |
| WO | 2009152456 A2 | 12/2009 |
| WO | 2010065836 A2 | 6/2010 |
| WO | 2010065886 A1 | 6/2010 |
| WO | 2010111705 A2 | 9/2010 |
| WO | 2012061804 A1 | 5/2012 |
| WO | 2012112931 A2 | 8/2012 |
| WO | 2012112934 A2 | 8/2012 |
| WO | 2012143274 A2 | 10/2012 |

OTHER PUBLICATIONS

Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).

Morris, "A shoe-integrated sensor system for wireless gait analysis and real-time therapeutic feedback," Harvard—MIT Division of Health Sciences and Technology, 2004,http://dspace.mitedu/handle/1721.1/28601 (3 pages).

Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/abstract (1 page).

Llosa et al., "Design of a Motion Detector to Monitor Rowing Performance Based on Wireless Sensor Networks," Intelligent Networking and Collaborativge Systems, 2009, http://ieeexplore.ieee.org/xpl/freeabs_all.jsp? arnumber=5369324 (1 page).

Frazier, Karen, "How Many Calories to 1 Carb?" published Nov. 12, 2010, Livestrong.com, 3 pages.

Jul. 31, 2012—(WO) ISR & WO—App. No. PCT/US12/025667.

Danko; How to Work a Nike Sensor; Dec. 26, 2010; eHow website; 4 pages.

Coyne; Stout's Shoes on Mass Ave Oldest Shoe Store in the USA; Jun. 18, 2013; FunCityFinder website; 5 pages.

Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.

Fleming et al., Athlete and Coach Perceptions of Technology Needs for Evaluating Running Performance, article, Aug. 14, 2010, 18 pages, 13:1-18, UK.

Morris, Stacy J., A Shoe-Integrated Sensor System for Wireless Gait Analysis and Real-Time Therapeutic Feedback, dissertation, 2004, pp. 1-314, Massachusetts Institute of Technology, MA.

Sep. 25, 2012—(WO) ISR & WO—App. No. PCT/US12/025713.

Jul. 15, 2013—(WO) Search Report and Written Opinion—App. No. PCT/US2013/022219.

Mar. 7, 2012—(WO) ISR & WO—App. PCT/US2011/060187.

Aug. 21, 2012—(WO) ISR and WO—App. No. PCT/US2012/025717.

Jul. 11, 2012—(WO) ISR & WO App No. PCT/US2012/025709.

Aug. 29, 2013—(WO) International Preliminary Report on Patentability App No. PCT/US2012/025713.

May 28, 2013—(WO) ISR & WO App No. PCT/US2013/027421.

Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).

Chee et al., "A low cost wearable wireless sensing system for upper limb home rehabilitation," Robotics Automation and Mechatronics (RAM) 2010 IEEE Conference on Jun. 28-30, 2010; Abstract printout (1 page).

Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).

Jun. 21, 2012—(WO) ISR—App No. PCT/US2012/025701.

Oct. 1, 2013—(WO) ISR and WO—App No. PCT/US2013/048157.

International Preliminary Report on Patentability for International Application No. PCT/US2009/035877, dated Sep. 16, 2010, 7 pages.

(56) References Cited

OTHER PUBLICATIONS

Apr. 25, 2012—(EP) European Search Report—App. No. 11 195 591.0.
May 11, 2010—(WO) International Search Report—App. No. PCT/US2009/066819.
Jun. 15, 2010—(WO) International Search Report—App. No. PCT/US2009/066745.
Apr. 1, 2014—(EP) Extended EP Search Report—App. No. 13196123.7.
Oliver Birbach et al, "Realtime perception for catching a flying ball with a mobile humanoid", Robotics and Automation (ICRA), 2011 IEEE International Conference on, IEEE, May 9, 2011 (May 9, 2011), pp. 5955-5962, XP032033950.
Jinchang Ren et al: "Real-Time Modeling of 3-D Soccer Ball Trajectories From Multiple Fixed Cameras", IEEE Transactions on Circuits and Systems for Video Technology, vol. 18, No. 3, Mar. 1, 2008 (Mar. 1, 2008),pp. 350-362, XP055100539.
Stefan Schiffer et al: "Qualitative World Models for Soccer Robots", Qualitative Constraint Calculi,, URL:<http://www-kbsg.informatik.rwth-aachen.de/sites/kbsg/files/schifferFL06kiqcc.pdf Jun. 14, 2006 (Jun. 14, 2006), pp. 1-12.
Oliver Birbach: "Accuracy Analysis of Camera1-Interial Sensor-Based Ball Trajectory Prediction", Diploma thesis, Universiry of Bremen, Feb. 13, 2008(Feb. 13, 2008), http://www.informatik.uni-bremen.de/agebv2/downloads/published/birbach_thesis_08.pdf.
Jun. 13, 2014—(WO) ISR and WO—App. No. PCT/US2013/066841.
Sep. 16, 2010—International Preliminary Report on Patentability for International Application No. PCT/US2009/035877.
Jul. 2, 2009—(WO) International Search Report and Written Opinion—App. No. PCT/US2009/35877.
United States District Court Southern District of New York (Foley Square), "Complaint (w/o exhibits)", *NIKE, Inc.* v. *Lululemon Athletica Inc et al.*, Case 1:22-cv-00082, filed Jan. 5, 2022, 29 pages.
United States District Court Southern District of New York (Foley Square), "Answer", *NIKE, Inc.* v *Lululemon Athletica Inc. et al.*, Case 1:22-cv-00082, filed Jan. 14, 2022, 15 pages.
United States District Court Southern District of New York (Foley Square), "Docket", *NIKE, Inc.* v. *Lululemon Athletica Inc. et al.*, Case 1:22-cv-00082, printed Jul. 26, 2022, 8 pages.
United States District Court Southern District of New York (Foley Square), Defendant's "Disclosure of Preliminary Invalidity Contentions", *NIKE, Inc.* v. *Lululemon Athletica Inc. et al.*, Case 1:22-cv-00082, filed Jul. 18, 2022, 1097 pages.
United States District Court Southern District of New York (Foley Square), Defendant's "Amended Exhibits", (Exhs. D-1, E-1, E-2, E-3, E-4, E-5, E-6) *Nike, Inc.* v. *Lululemon Athletica Inc. et al.*, Case 1:22-cv-00082, filed Jul. 26, 2022, 183 pages.
David R. Bassett, Jr., Validity and Reliability Issues in Objective Monitoring of Physical Activity, Research Quarterly for Exercise and Sport, vol. 71, No. 2, pp. 30-36 (2000) ("Bassett"), 7 pages.
Chris Hall, Nokia Sports Tracker, Pocket-lint (Jul. 25, 2008), https://www.pocket-lint.com/phones/reviews/nokia/70414-nokia-sports-tracker-mobile-application ("Hall"), 11 pages.
Jozsef Hajdu, Provided Services of Social Networks for Sport, TKK T-110.5190 Seminar on Internetworking (Apr. 28-29, 2008), http://www.cse.tkk.fi/en/publications/B/1/papers/Hajdu_final.pdf ("Hajdu"), 8 pages.
Zee, Breaking: Goodbye Twitter? Facebook adds ©mentions to status updates (Sep. 10, 2009, 9:16 PM), https://thenextweb.com/news/breaking-facebook-adds-mentions-status-updates?amp=1 ("Zee"), 6 pages.
Robert Anderson (@rsa), Twitter (Nov. 2, 2006, 11:58 PM), https://twitter.com/rsa/status/55281?lang=en ("Anderson"), 3 pages.
Scott Tousignant (@TheFitB), Twitter (Nov. 27, 2008, 12:27 PM), https://twitter.com/TheFitB/status/1026679285 ("Tousignant"), 1 page.
Internet webpage wii.nintendo.com/controller.jsp, dated Nov. 30, 2006 and retrieved from the Internet Archive ("Nintendo webpage").

\* cited by examiner

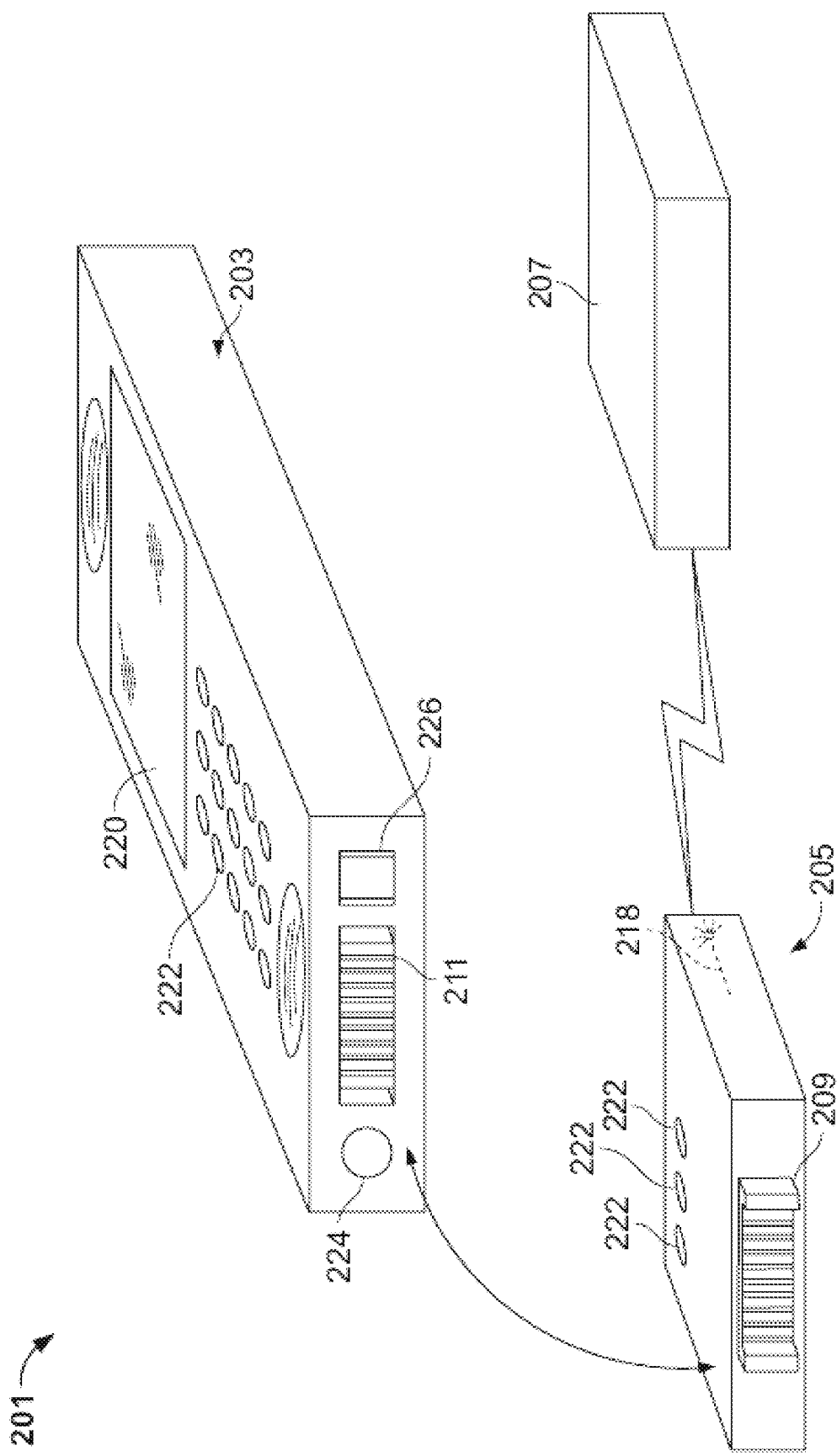

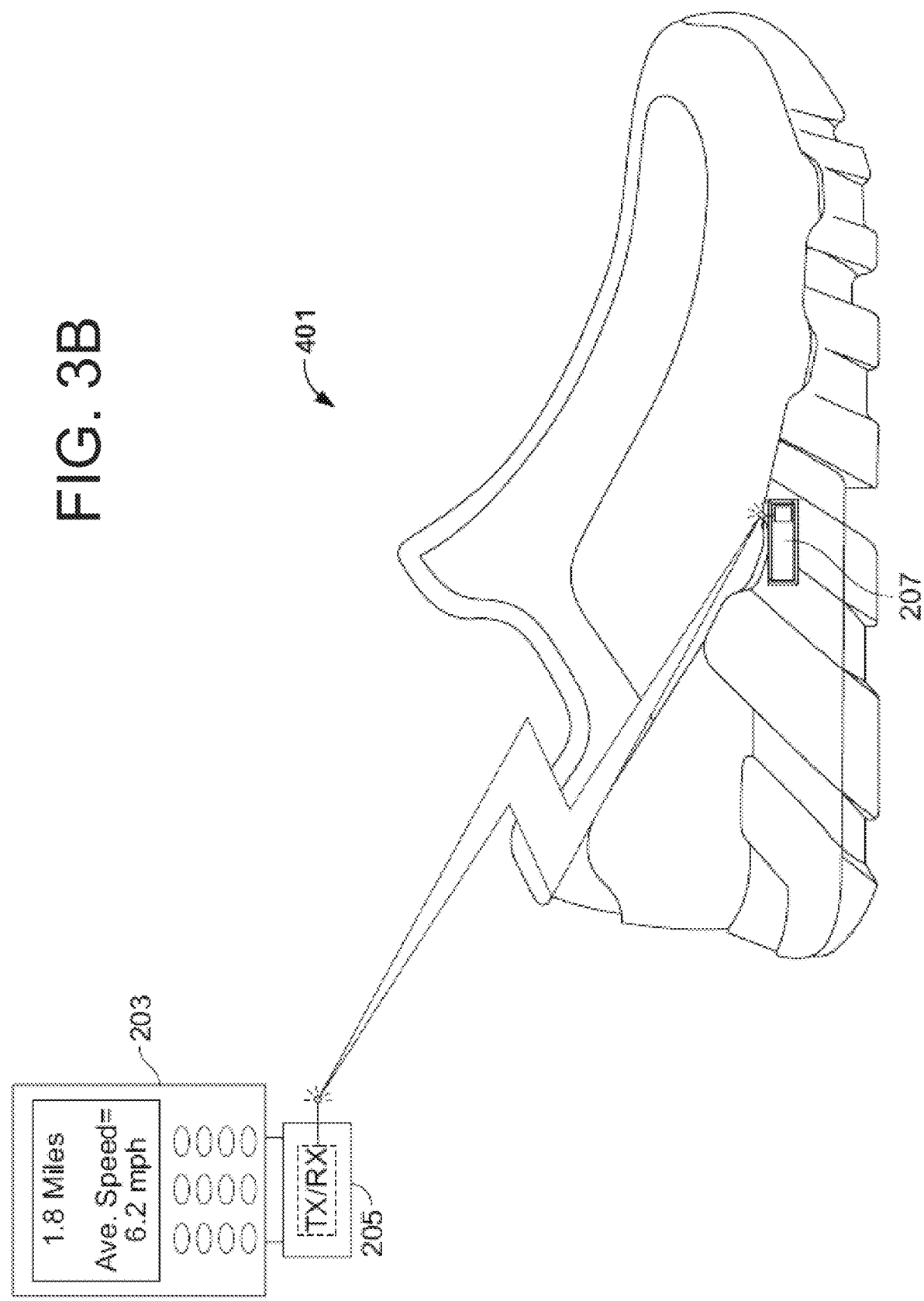

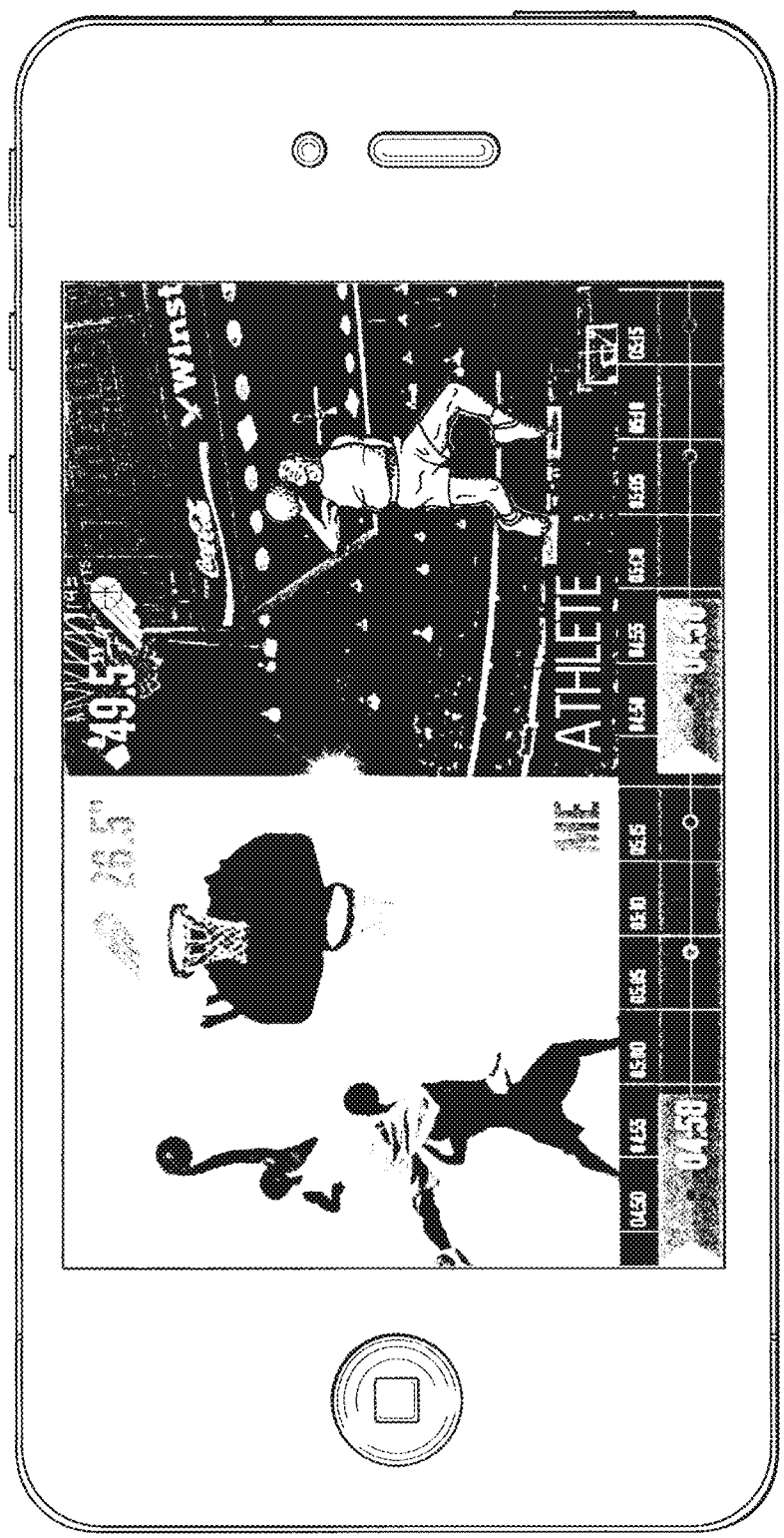

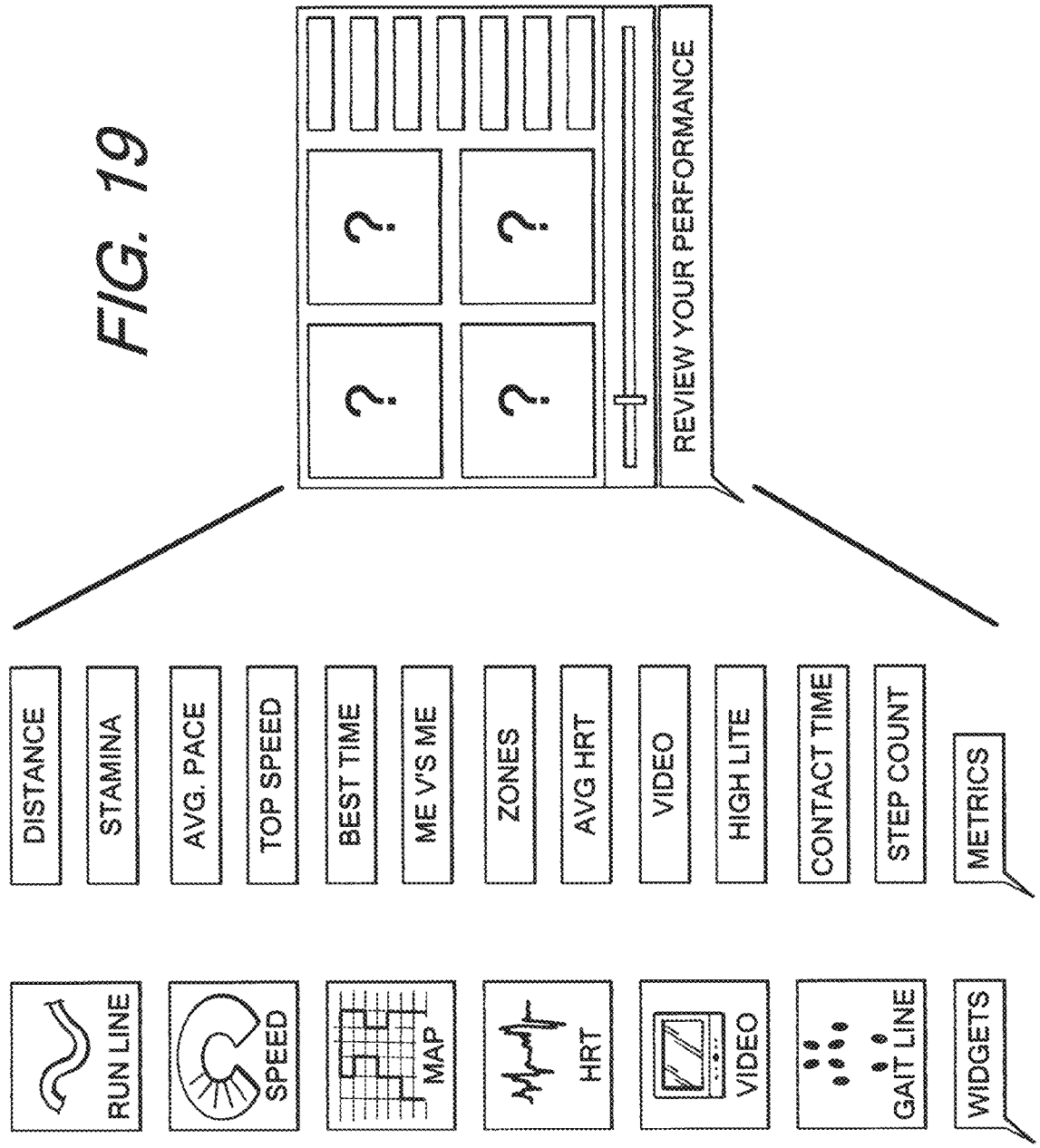

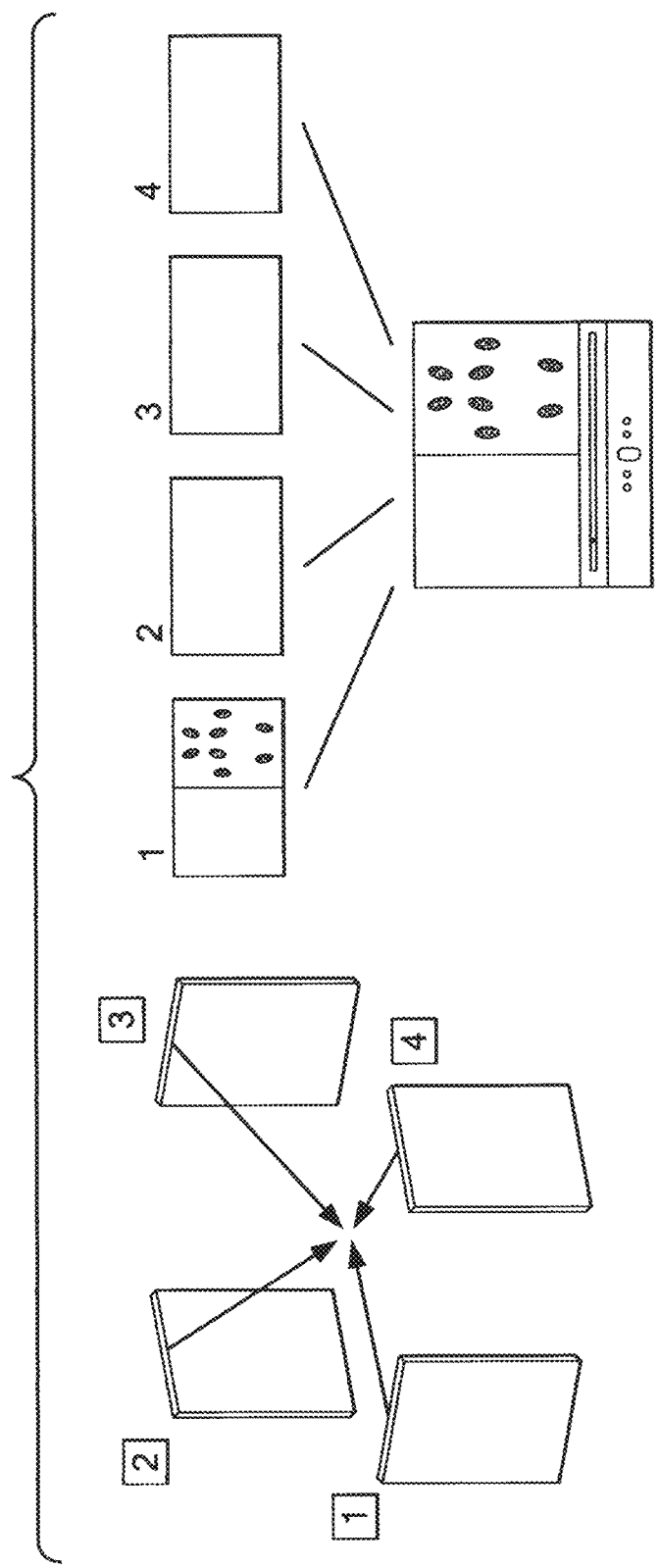

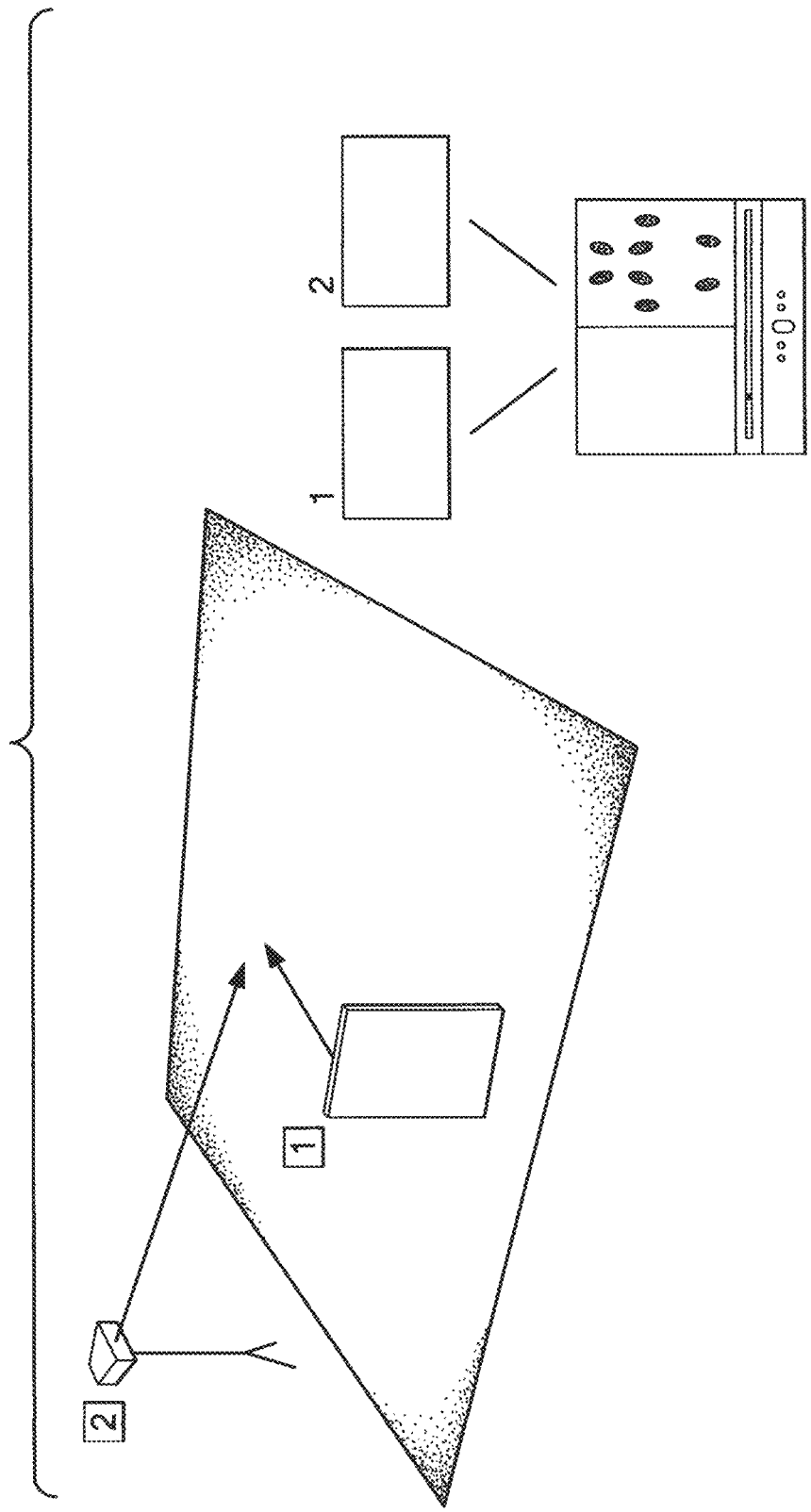

_US 11,600,371 B2_

SYSTEMS AND METHODS FOR TIME-BASED ATHLETIC ACTIVITY MEASUREMENT AND DISPLAY

CROSS-REFERENCE TO RELATED APPLICATION

This application is a continuation of U.S. patent application Ser. No. 16/376,123, filed Apr. 5, 2019, now U.S. Pat. No. 10,632,343, which is a continuation of U.S. patent application Ser. No. 15/994,517, filed May 31, 2018, now U.S. Pat. No. 10,293,209, which is a continuation of U.S. patent application Ser. No. 15/693,753, filed Sep. 1, 2017, now U.S. Pat. No. 10,010,752, which is a divisional of U.S. patent application Ser. No. 15/223,188, filed Jul. 29, 2016, now U.S. Pat. No. 9,757,619, which is a divisional of U.S. patent application Ser. No. 14/722,695, filed May 27, 2015, now U.S. Pat. No. 9,429,411, which is a continuation of U.S. patent application Ser. No. 14/478,203, filed Sep. 5, 2014, now U.S. Pat. No. 9,389,057, which is a continuation of U.S. patent application Ser. No. 13/293,653, filed Nov. 10, 2011, now U.S. Pat. No. 8,831,407, which claims the benefit of U.S. Provisional Application No. 61/412,285, filed Nov. 10, 2010, the contents of which are incorporated herein in their entirety for any and all non-limiting purposes.

TECHNICAL FIELD

The invention relates generally to recordation and visualization of athletic activity. In particular, aspects described herein relate to time-based recordation and review of athletic activity and time-specific metrics associated therewith.

BACKGROUND

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide performance data or to keep them in contact with others, etc. Such users have also demonstrated an interest in recording their athletic activities and metrics associated therewith. Accordingly, various sensors may be used to detect, store and/or transmit athletic performance information. Oftentimes, however, athletic performance information is presented in a vacuum or based on the overall athletic activity. Athletic performance data might not be readily available for a particular period or instance of time during the athletic activity session. As such, users might not be able to identify specific times or time periods within their workout or other athletic activity that certain metrics or performance statistics were achieved.

A full discussion of the features and advantages of the present invention is referred to in the following detailed description, which proceeds with reference to the accompanying drawings.

SUMMARY

The following presents a general summary of aspects of the invention in order to provide a basic understanding of at least some of its aspects. This summary is not an extensive overview of the invention. It is not intended to identify key or critical elements of the invention or to delineate the scope of the invention. The following summary merely presents some concepts of the invention in a general form as a prelude to the more detailed description provided below.

One or more aspects describe systems and methods for tracking athletic activity metrics based on a timeline. Metrics may be recorded continuously or based on a predefined schedule. In either case, multiple values may be recorded for the same metric and associated with the particular time period or specific time at which the values were detected. For examples, athletic performance data may be detected and recorded for every minimum time unit. The minimum time unit may correspond to 1 second, 2 seconds, a millisecond, 10 seconds and the like. Using such time-based recordings, the user may review instantaneous and specific metric values to determine how they were performing at particular points during their athletic activity performance.

According to another aspect, users may display the multiple metrics simultaneously in an interface during review of the athletic activity session. For example, a user may display a video in a primary visualization area with overlays of one or more desired metrics. Additionally or alternatively, a toolbar may be displayed to provide other metrics not currently displayed in the primary visualization area.

According to yet another aspect, the multiple metrics may be recorded using multiple different applications or widgets. A user may select which metrics and/or widgets to use prior to the athletic activity session or prior to initiation of recordation. The user may also modify the selected metrics or applications during session recordation.

According to still another aspect, a user may edit the collected data prior to or after the metrics and other data are compiled into a single athletic activity session file of electronic content item (e.g., an enhanced video). For example, the user may remove metrics from being included in the athletic activity session file even if the metrics have already been recorded. Additionally or alternatively, the user may crop a video or other metrics to a desired period of time (e.g., smaller than the overall duration of the athletic activity session).

According to yet another aspect, a plurality of video segments of an athletic activity session of a user may be captured by a plurality of video sources. A processing system may determine that each of the plurality of video segments correspond to the athletic activity session of the user, and, accordingly, the processing system may generate a video replay of the athletic activity session of the user by piecing together the plurality of video segments captured by the plurality of video sources. The first portion of the video replay includes a first video segment captured by a first video source of the plurality of video sources, and a second portion of the video replay includes a second video segment captured by a second video source of the plurality of the video sources different than the first video source.

According to yet another aspect, an athletic parameter measurement device configured to by worn by an athlete during an athletic activity session detects and displays one or more metrics during the athletic activity session. For example, the athletic parameter measurement device may include a housing with an attachment mechanism configured to be attached to the athlete during the athletic activity session, a display, a processor associated with the display, and at least one athletic parameter measurement sensor. The device may be configured to detect, by the at least one athletic parameter measurement sensor, at least one metric of the athlete during the athletic activity session while the housing is worn by the athlete, wherein the at least one metric of the athlete includes a vertical jump height of the athlete, transmit, by the at least one athletic parameter measurement sensor to the processor, the at least one metric, and display, by the processor on the display, during performance of the athletic activity session, a representation of the at least one metric.

Other aspects and features are described throughout the disclosure.

BRIEF DESCRIPTION OF THE DRAWINGS

To understand the present invention, it will now be described by way of example, with reference to the accompanying drawings in which:

FIG. 2 illustrates an example computing device that may be used according to one or more aspects described herein;

FIGS. 3A and 3B illustrate example sensor and monitoring device communication environments according to one or more aspects described herein;

FIGS. 17A-17D illustrate example interfaces configured to display a comparison between two activity sessions and/or athletes according to one or more aspects described herein;

FIG. 19 illustrates the editing of metric data upon compiling an activity session file according to one or more aspects described herein; and FIGS. 20 and 21 illustrate example environments in which multiple video or data capture sources may be used according to one or more aspects described herein.

DETAILED DESCRIPTION

In the following description of various example embodiments of the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention. Also, while the terms "top," "bottom," "front," "back," "side," and the like may be used in this specification to describe various example features and elements of the invention, these terms are used herein as a matter of convenience, e.g., based on the example orientations shown in the figures. Nothing in this specification should be construed as requiring a specific three dimensional orientation of structures in order to fall within the scope of this invention.

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Example Hardware Devices

Figure 1:
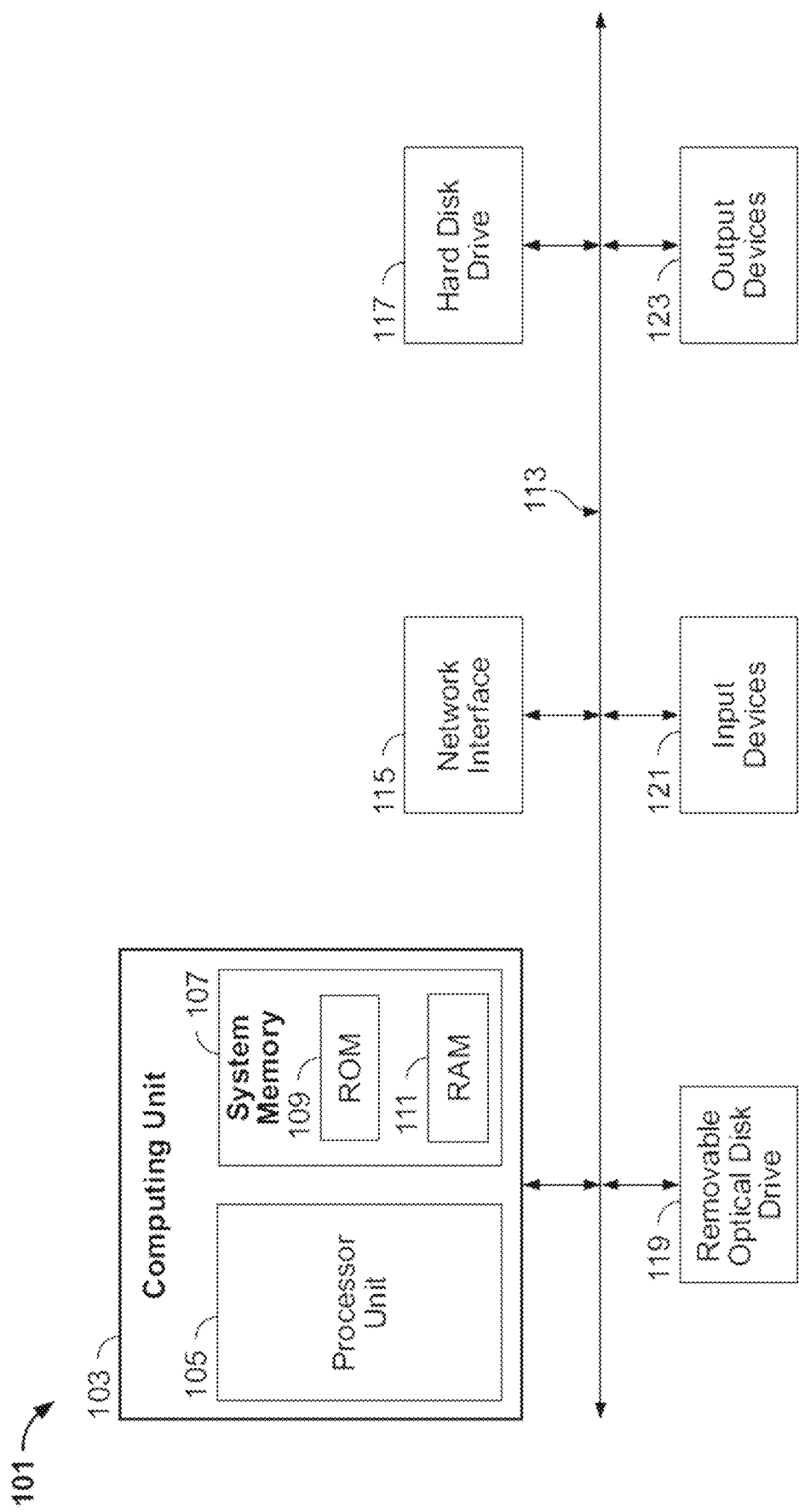
FIG. 1 illustrates an example computing environment in which one or more aspects described herein may be used.

FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can server as both an output device for a computer (e.g., outputting music from a sound file or pictures from an image file) and a storage device. In addition, this type of digital music play also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, in one embodiment, the digital music player 203 may be (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203. In some arrangements, electronic interface device 205 might not be used if digital music player 203 or other electronic device is capable of interfacing with measurement device 207 directly. For example, the athletic parameter measurement device 207 may be configured to communicate using the Bluetooth wireless communication protocol, so that it can be employed with Bluetooth-capable mobile telephones, personal digital assistants, watches or personal computers.

Figure 3A:
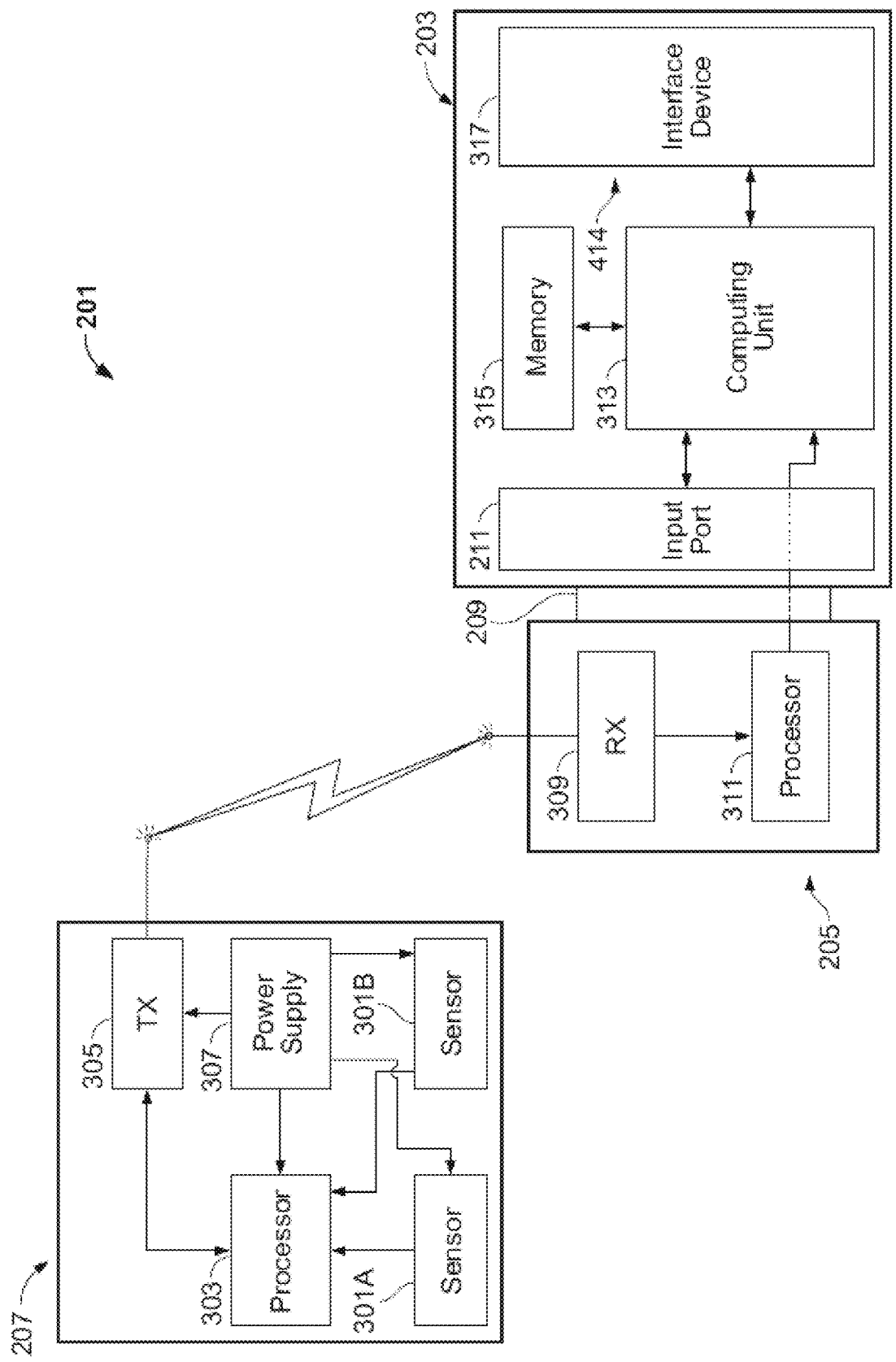

As shown in more detail in FIG. 3A, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 3B, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 307. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 3B. Returning now to FIG. 3A, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3A, the processor 311 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the between the athletic parameter measurement device 207 and the interface device 205 is described for the embodiments illustrated in FIGS. 2-3B, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, anther type of music player (such as a compact disc or satellite radio music player), a portable computer, or any other desired electronic device.

Figure 3C:
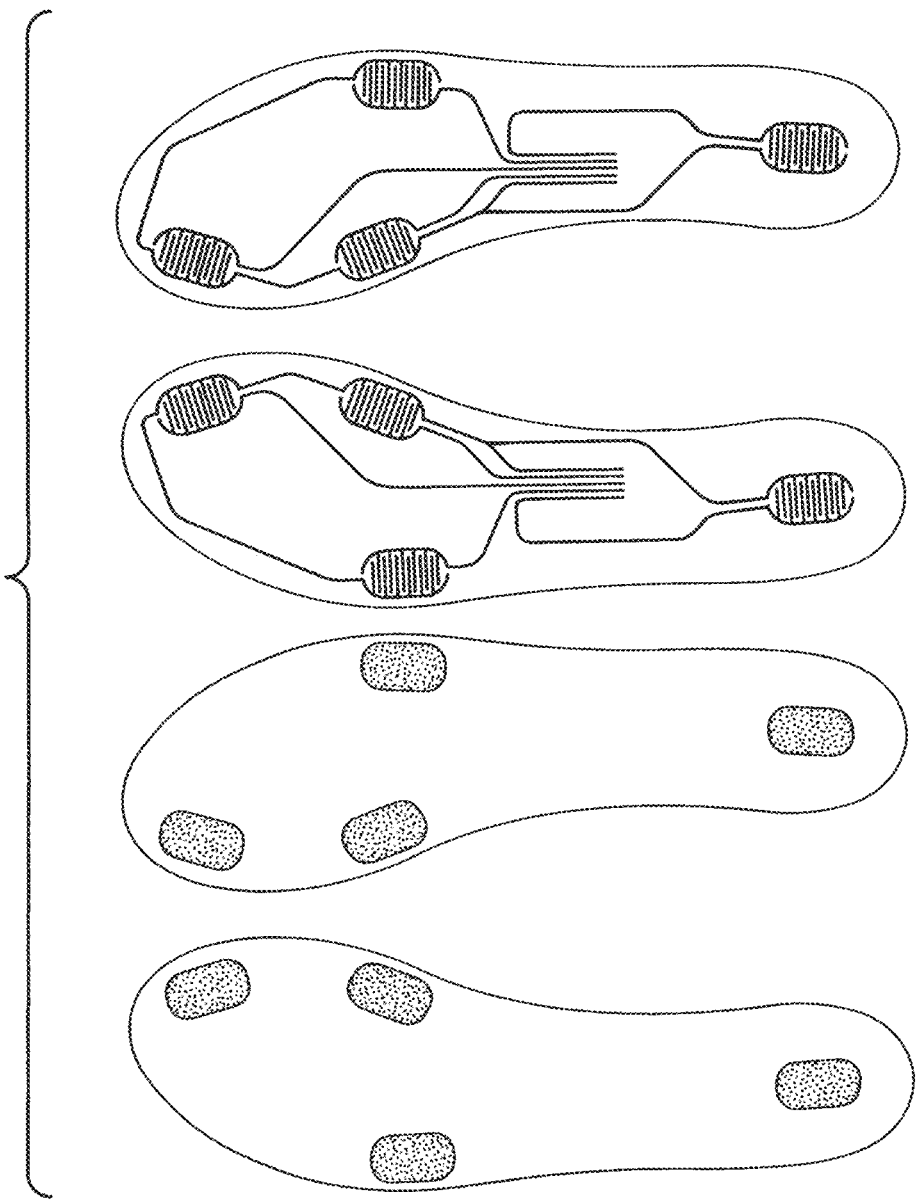
FIG. 3C illustrates an example shoe sensor system having force sensing capabilities according to one or more aspects described herein.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc. Other types of sensors may include strain gages, temperature sensors, heart-rate monitors and the like. In one or more arrangements, a user may equip multiple sensors and, in some instances, the same type of sensor in multiple locations. For example, users may wear shoes that are each equipped with an accelerometer, weight sensor or the like, in order to allow a system to determine the individual movement and metrics of each foot or other body part (e.g., leg, hand, arm, individual fingers or toes, regions of a person's foot or leg, hips, chest, shoulders, head, eyes). Examples of multi-sensor apparel and the use of multiple sensors in athletic activity monitoring are described in U.S. application Ser. No. 12/483,824, entitled "FOOTWEAR HAVING SENSOR SYSTEM," and published as U.S. Publication No. 2010/0063778 A1 and U.S. application Ser. No. 12/483,828, entitled "FOOTWEAR HAVING SENSOR SYSTEM," and published as U.S. Publication No. 2010/0063779 A1. The content of the above reference applications are incorporated herein by reference in their entirety. In a particular example, an athlete may wear having one or more force sensing systems, e.g., that utilize force-sensitive resistory (FSR) sensors. The shoe may include multiple FSR sensors that detect forces at different regions of the user's foot (e.g., a heel, mid-sole, toes, etc.). This may help determine balance of a user's foot or between a user's two feet. In one exemplary embodiment, a FSR sensor array may take the form such as shown in FIG. 3C.

Also, while the athletic parameter measurement device 207 has been described as being separate from the digital music player 203 or other portable electronic device that receives the signals from the athletic parameter measurement device 207, with some implementations of the invention the athletic parameter measurement device 207 may be incorporated into or integrated with the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Time-Based Data Collection

Athletic performance monitoring systems such as digital music player 203 or interface 205 of FIG. 2 may be used to collect, edit, store and share athletic performance data as measured by one or more external or internal sensors. This athletic performance data may be collected over a period of time that the user is performing an activity. To provide data specificity and flexibility in the use of the data, the monitoring system may collect data several times during the course of the athletic activity. In one example, the monitoring system may collect and store athletic data at every minimum time unit. For example, the minimum time unit may correspond to every second that the user is engaged in the athletic activity. In another example, the monitoring system may collect and store athletic data for every 0.5 seconds, 5 seconds, 10 seconds, 30 seconds, minute or the like. The data collected may then be mapped, associated and/or otherwise stored with the corresponding instant in time or time period in which the data was captured. The minimum time unit may be defined by the user or the system or may be defined based on a minimum time unit that is used to record video or audio of the activity session. For example, if a video provides playback granularity at the half second level, the system may record performance data at every half second. In another example, if a video is recorded at 30 frames per second, the system may record performance data (e.g., metrics) every $\frac{1}{30}^{th}$ of a second to match each frame of video.

Figure 4:
FIG. 4 is a flow diagram illustrating the features of a time-based athletic performance monitoring system according to one or more aspects described herein.

FIG. 4 illustrates a general process by which a user may collect and user athletic performance data. For example, the user may initially capture desired metric data. For example, a user may select or otherwise specify the type of metric that he or she wishes to record during an athletic activity session. In one example, the user may select metrics by selecting or deselecting individual types of metrics from a user interface. In another example, the user may select metrics by identifying a previous recorded set of athletic performance data and indicating that he or she wishes to record the same metrics as the previous athletic performance data set. Metric data may include video, audio, speeds, paces, reaction times, jump height, locations (e.g., using a GPS sensor or cellular triangulation), sweat level, body temperature, reach distance, weight lifted, strength and the like. Once captured, the user may edit the data, share the data and motivate himself or herself and/or others (e.g., by attempting to beat the one or more metrics of a previously recorded activity session).

Figure 5:
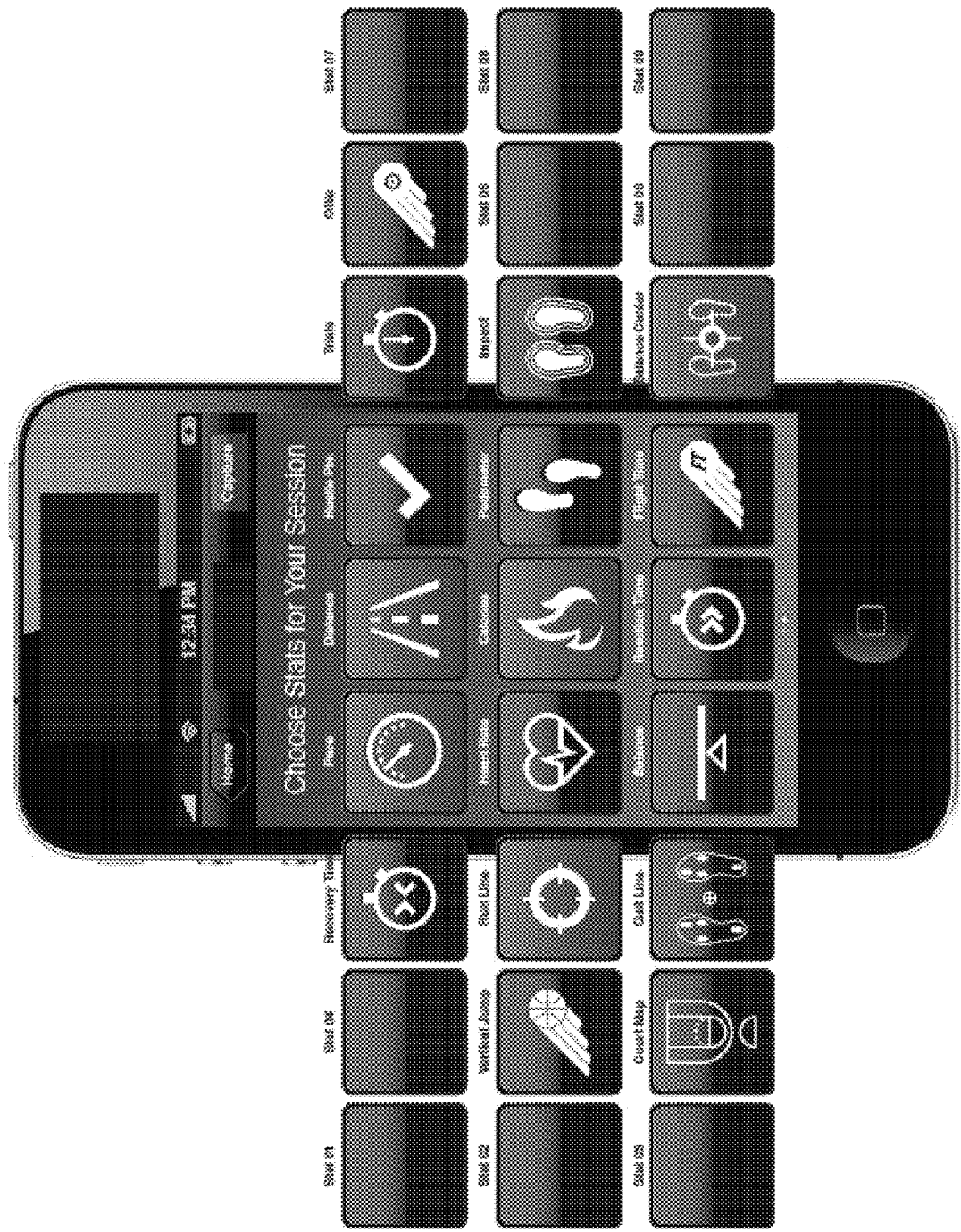
FIG. 5 illustrates an example metric/application selection interface according to one or more aspects described herein.

Many different types of metrics may be measured and recorded in association with a time at which the metric was detected. FIG. 5 illustrates an example user interface through which a user may select various time-specific metrics to record. Other metrics may still be recorded for an athletic activity even if not selected, however, those other metrics might only be recorded as an average over the entire workout (e.g., rather than storing the metric information at the same level of granularity (e.g., 1 second, 2 seconds) as the selected metrics). Accordingly, selected metrics may be detected, recorded and/or stored at a first level of granularity (e.g., a first speed—every second, every 2 seconds, every 30 seconds, every millisecond, etc.) while non-selected metrics may be detected, recorded and/or stored at a second level of granularity (e.g., every 2 minutes, every 10 minutes, every 15 minutes), where the first level of granularity is greater than the second level of granularity. For some metrics that correspond to a period of time (e.g., pace), the metric may be recorded for a specified period of time (e.g., 2 seconds) and associated with every time unit of that period (e.g., a pace of 7.8 mi/hour over 2 seconds is recorded for and associated with each second of those 2 seconds). As such, the other metrics might not be specific to (or recorded as being specific to) any particular time or time period (e.g., a time period smaller than the entire workout/activity duration, a minimum time unit, etc.) during the workout. Each of the selectable metrics displayed in FIG. 5 may correspond to and be recorded by an application or applet (e.g., a widget). In one arrangement, each metric widget or application may be configured to measure and record a particular set of one or more metrics along a timeline. For example, each metric widget or application may be specific to the corresponding metric that the widget or application is configured to record. The timelines for multiple metric widgets or applications may then be merged to consolidate the metric data into a single activity session based on their timelines. Generally, the timelines of the various widgets or applications will match one another since the recording is likely to be initiated at the same time.

Metric applications or widgets may be created by athletes or other users. In one example, the metric applications may be available through a marketplace or community where users may download new and/or updated metric applications. The application may include algorithms, instructions, visual features, functional elements that are specific to the particular metric and application. Thus, in one or more arrangements, a metric selection interface may include multiple different applications or applets for the same type of metric. In one example, celebrations, messages, interface functionalities may be defined by users for various types of metrics. In a particular example, a vertical (e.g., jump height) widget may include a celebration once the user reaches a 2 foot jump height while a pace widget may include a celebration that is provided once the user achieves a 7 minute mile pace.

As illustrated in FIG. 5, metrics may include recovery time, pace, vertical jump, court map, gait line, run line, heart rate, balance, distance, calories, reaction time, hustle points, pedometer, flight time, trials, ollie, impact and balance center. For example, recovery time may be a measure of how long a user is motionless or exhibits a level of activity or motion below a certain threshold. This time may be considered time the user is spending to recover or rest. A court map, on the other hand, may plot the user's position against an athletic activity court or field or other predefined space. For example, if a user is playing basketball, a virtual representation of a basketball court may be generated and displayed along with a user's movement around the virtual court. In another example, football players may be graphed around a virtual football field. Reaction time, on the other hand, may measure the amount of time between two events such as a ball bouncing on a rim and the user jumping up to grab the ball (e.g., a rebound reaction time). In another example, a basketball player's reaction time to a pass may be measured between a time at which the ball is released from another player's hands and the instant the user makes a move toward the ball (e.g., as measured by hip movements or directional movement of hands or body). Hustle points may be awarded in a variety of manners including based on a speed of an athlete in completing objectives, reaching an object (e.g., a ball), moving a predefined amount of distance, moving from one specified point to another and the like. In one example, hustle points may be awarded for each second a user is moving at a speed above a threshold speed (e.g., 0.5 points per second above 10 mph).

An athletic monitoring system may determine flight time or air time by measuring the time between a user's feet leaving a floor and a time at which the user's feet touch the ground. Flight time or air time may also be measured based on other body parts or devices including skateboards (e.g., skateboard flight time) or between hands and feet (e.g., for a back flip). Flight or airtime for certain activities may have their own metric such as number of ollies for skateboarding. The ollie metric may use different parameters to measure the airtime of the skateboard trick. In yet another example, air time for the ring exercise in gymnastics may be measured based on when a user's hands leave the rings and when the user's hands return to the rings or the user's feet land on the ground. Various other flight time or air times may be defined based on various body and device sensors.

Impact may represent an amount of force that a user exerts. In one example, a boxing activity may be measured for impact of a user's fist when punching. In another example, a user's impact upon landing may be measured in basketball. In yet another example, a user's impact upon hitting or tackling another user may be measured to determine an effectiveness or strength in football. Gait line and run line may measure a user's direction or pattern of foot movement during walking or running, respectively. In other examples, the pattern or direction of movement for other body parts may also be measured and analyzed. According to one or more arrangement, a run line metric may identify a path a user takes during a run. The path may be determined using location determination system such as global positioning satellites and the like.

Balance and balance center both relate to the amount of weight being placed on each foot. In one example, balance may indicate a difference in weight being placed on each foot while balance center may provide an indicator that shows where the user's center of balance exists relative to the position of his feet.

Additionally or alternatively, the system may provide a trials metric configured to measure a user's performance for time. In a trial, the user is typically racing against the clock, trying to achieve the fastest time possible. Accordingly, the system may measure the user's trials and provide time information associated therewith.

Figure 6:
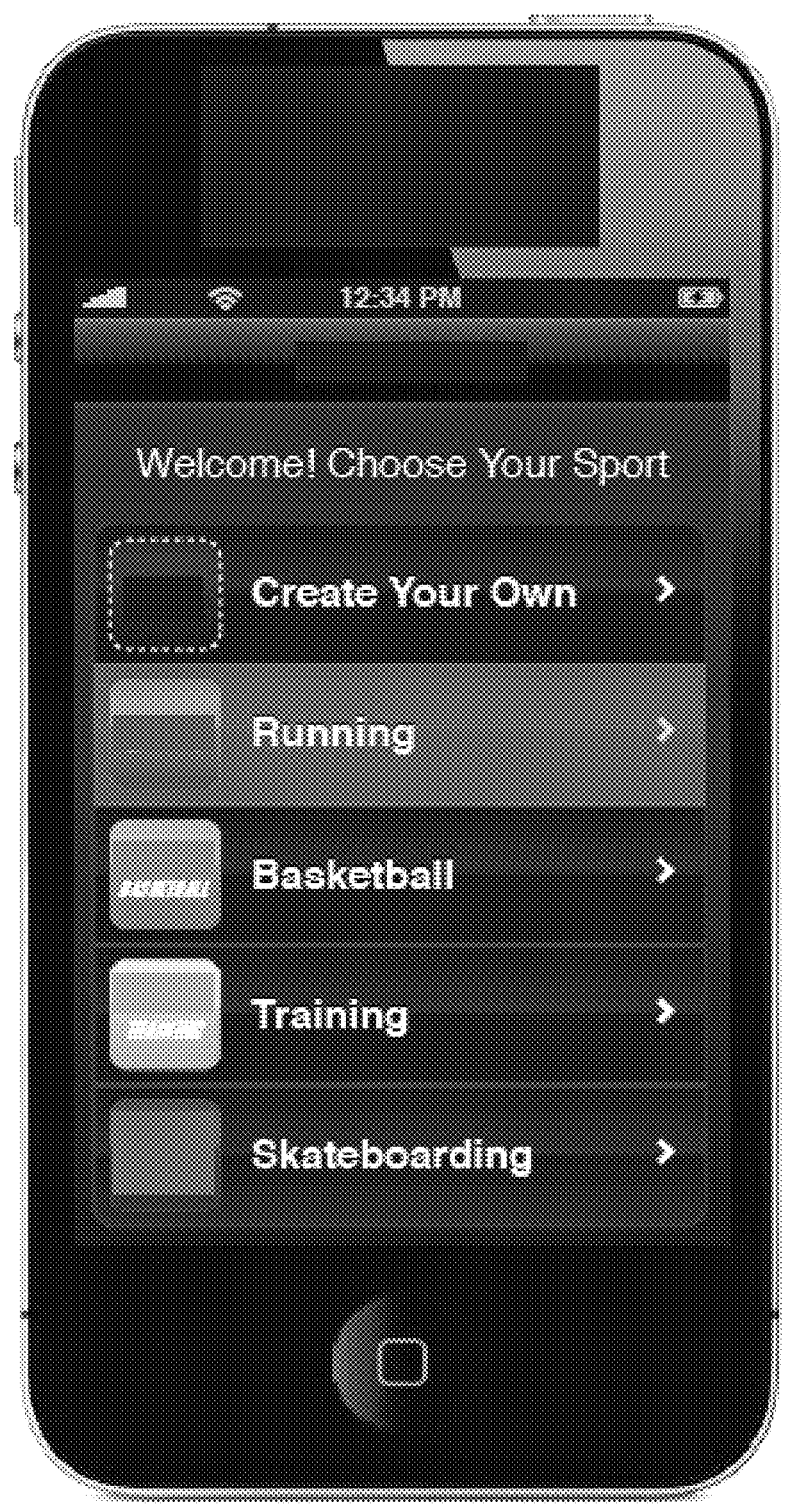
FIG. 6 illustrates an example activity selection interface according to one or more aspects described herein.

To simplify the use of the performance monitoring system and selection of metrics, one or more sets of metrics may be predefined. For example, a first set of one or more metrics may be pre-selected and/or defined for each of running, basketball, training and skateboarding as illustrated in FIG. 6. Accordingly, upon a user selecting one of the activity options or types, the corresponding set of metrics may automatically be chosen. In some arrangements, the corresponding set of metrics may be automatically chosen along with an activity-type specific widget or application configured to record the selected metrics and the activity of that type.

The user may be provided with an opportunity to customize the automatic selection after selecting the activity. Alternatively or additionally, the user may also choose to create a custom predefined set or to manually select the metrics that he or she wishes to use for a current activity (e.g., using the Create Your Own option). As noted above, a user may select a previously performed workout and ask to record the same metrics as the previously performed workout. Accordingly, the system may automatically extract the metrics recorded for the previously performed workout from an athletic performance data set associated with the previously performed workout. If a user customizes his or her own set of metrics, the user may choose to store and label the customized set. The customized set may then appear in a menu of predefined activities (e.g., as shown in FIG. 6) when the user next begins an activity session. While only basketball, running, training and skateboarding are listed as activities in FIG. 6, numerous other activities may also have predefined metric or widget sets and may similarly be displayed in such an interface. In fact, any type of motion may be tracked according to the features described herein including dancing, swimming, skipping rope, wrestling, public speaking (e.g., to track the amount of user hand motion or eye contact), traveling (e.g., number of steps taken during a trip, elevation change during the trip) and the like.

Furthermore, users may share customized metric or widget sets with other users. For example, a marketplace or share space may be created where users may exchange, purchase and/or download metric and widget sets from other users, services, coaches and the like. In one or more arrangements, metric and widgets sets may be shared among users with specific interests (e.g., skateboarding or swimming) or may be shared more generally. Other privacy and security parameters may also be defined including specifying whether the general public is allowed to download and view the metric set or if only a specified group (e.g., friends, community group, etc.) are allowed to view and download. In one or more aspects, a user may define their own metrics. In one example, a user may define a metric called "one-leg vertical height" for recording a height that a user is able to jump on one leg or foot. The user may define the metric may specifying the types of sensors to use, conditions for activating or deactivating the sensor and the sensor output that is to be detected. Accordingly the above user may indicate that the metric is only measured when sensors for one shoe are contacting a surface and the metric corresponds to half of an amount of time between detecting loss of contact between the one shoe and a surface and detecting subsequent contact of the same shoe with a surface.

Figure 7:
FIG. 7 illustrates an example recording initiation interface according to one or more aspects described herein.

FIG. 7 illustrates an example interface through which a user may initiate recording of an activity session upon selecting a set of desired metrics to be tracked. The interface may include a timeline on the bottom of the screen to indicate an amount of elapsed time since a start of the activity. A user may select the start your run/record option displayed in the middle of the screen to begin recording metrics and/or video for the activity. In one example, video may be recorded by the metric recording device (e.g., a video camera on a mobile telecommunication device or a laptop). As the data is recorded, the data (video and metrics) may be stored in association with the particular instant or time period during the activity session at which the data was captured. As noted previously, data may be collected substantially continuously (e.g., every 0.1 or 0.5 seconds, 1 second). Other recording intervals may be defined as well (e.g., every 2 seconds, 5 seconds, 10 seconds, 15 seconds, 5 minutes). The interface may further display a currently selected primary metric. The primary metric may be displayed a visualization space of the interface. For example, in FIG. 7, a run line is displayed in the visualization space (partially covered by the recording option). The user may pause or stop the recording using the corresponding options displayed in the header bar (e.g., on either side of the primary metric name).

Figure 8:
FIG. 8 illustrates an example interface displaying a user's recorded activity path and additional metrics according to one or more aspects described herein.

FIG. 8 illustrates an athletic performance monitoring interface that may be displayed upon a user beginning an athletic activity session. An icon in the header bar may indicate that the current activity and metrics thereof are being recorded. A primary visualization space may display a particular metric such as run path or run line in the illustrated example. In one arrangement, a user's current position on the map may be identified by an indicator. Other metrics may be displayed in a metrics bar. The metrics may update continuously or based on a specified schedule as the activity is being performed. For example, the user's pace (e.g., 7:46 miles) may be updated in real-time as a user gets faster or slows down. Similarly, a user's balance (currently showing 46% weight on the left foot and 54% of the user's weight on the right foot) may similarly be updated in real-time. The data shown may be the instantaneous data or the data may comprise an average of a previous amount of data (e.g., all previous data recorded for the session or a proper subset of data recorded for the session).

Other metrics may be displayed upon selecting one of the directional arrow options along the metrics bar (as will be described and illustrated in further detail below). Upon selecting one of the metrics in the metric bar, the primary visualization space may change to display the selected metric. The previously displayed metric may be returned to the metric bar (e.g., replacing the newly selected metric/widget). Furthermore, a current elapsed time may be displayed against the timeline. Additionally, an amount of elapsed time may be represented in the timeline by a different color or appearance (e.g., red, polka-dots, stripes, blue, green, etc.).

Figure 9:
FIG. 9 illustrates another example activity selection interface according to one or more aspects described herein.

FIG. 9 illustrates another example activity selection interface having a basketball activity highlighted or in the process of being selected. As noted herein, different activities may correspond to different sets of metrics. In one example, a basketball metric may include video and/or audio recording. Accordingly, selection of the basketball activity may activate a video recording function.

Figure 10:
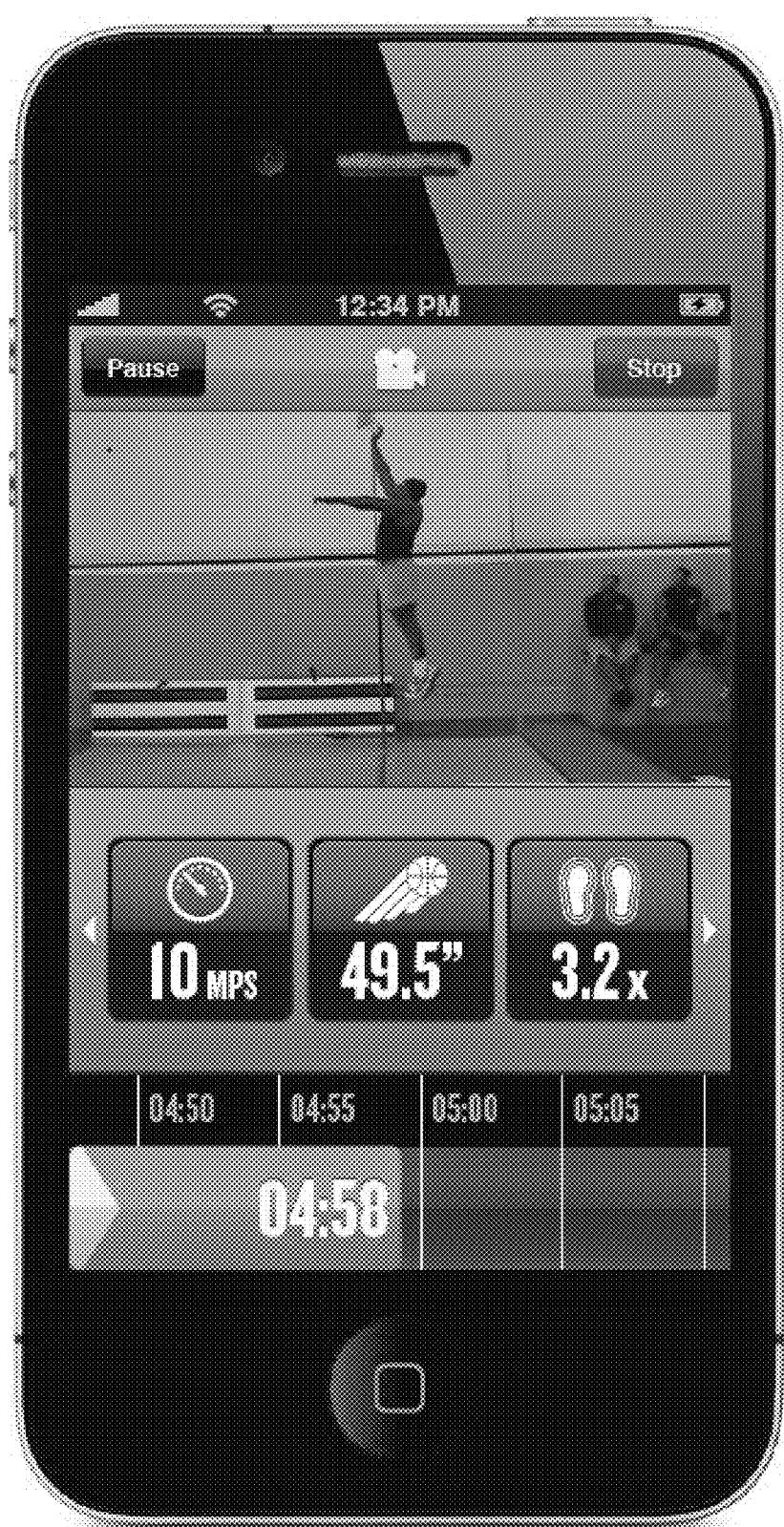
FIG. 10 illustrates an example interface displaying video of a user's recorded activity, a timeline and other metrics in a metric toolbar according to one or more aspects described herein.

FIG. 10 illustrates an example metric monitoring interface in which video is recorded for a basketball activity. A basketball activity may include activities related to training for or improving skills related to basketball and is not necessarily limited to a basketball game. Similar training or evaluation type activities might also be monitored for other sports and activities as well. As the video is being recorded, other metrics as shown in the metrics bar may also be recorded at the same time and associated with a time at which the data was captured. The metric or metric widget being displayed in the primary visualization space may be modified by selecting a different metric from the metric toolbar. The video may continue to be recorded and displayed in the metric widget on the metric toolbar. Metrics toolbar may include metrics widgets such as a pace metric widget, a vertical jump widget and an impact widget. The vertical jump widget may measure a user's vertical ground clearance at the particular point in time while the impact widget may measure the amount of force exerted by a user's feet (e.g., upon landing) or hands (e.g., for blocking a shot) or an amount of force with which a ball was shot or thrown. The pace metric for a basketball activity may measure acceleration in a vertical or horizontal direction (e.g., instead of measuring mile pace). The metrics shown may be specific to the instant identified in the timeline, i.e., 4 minutes and 58 seconds into the athletic activity session. Alternatively or additionally, one or more of the metrics shown may be an average of the metrics up to the instant identified in the time line (e.g., an average over the first 4 minute and 58 seconds).

Data collection may also be facilitated by including identifiers in one or more sensors or other wearable device (e.g., shoe, gloves, headgear, etc.). A metric capturing device such as a video camera or speed camera may automatically adjust direction and focus based on finding the appropriate subject using the identifier and determining its location. In other arrangements, identifiers or wearable identifier tags might not be necessary. A camera or other sensor device may automatically determine the location of a desired subject based on image recognition (e.g., facial recognition or body recognition). Using identifiers, data may also be displayed as an overlay near or proximate to the corresponding sensor, person or person's body part. For example, step information may be displayed near a user's foot during video playback by detecting the position of the user's foot through the identifier. In another example, multiple sets of metrics may be displayed for the multiple individuals displayed in a video. Accordingly, the identifiers may be used to place the metrics close to the appropriate individuals.

Video collection may also be facilitated by combining videos from multiple different video sources as shown in FIG. 21. For example, multiple individuals may use their video camera to record the same event (e.g., a soccer game or a dance competition). A processing system may detect that each of the multiple videos corresponds to the same event and piece the videos together to fill in gaps between the individual videos. Additionally, the system may insure that the video maximizes images of a desired subject. Again, body or facial recognition may be used to identify particular subjects and to assemble portions having the desired subject or subjects together into a single video. Each portion may have a duration that corresponds to a sub-time period of the duration or overall time period of the source video or content item. The use of multiple cameras or video streams may also allow an individual to view a subject (e.g., himself or herself, a child, a player, etc.) from multiple angles and, in some instances, in 3-D.

According to another aspect, video recording by location-specific cameras and other recording equipment may be automatically triggered based on detection of an identifier or other electronic tag. FIG. 21, for instance, illustrates a location such as a gym or park with a camera 2 that belongs to or is otherwise associated with the location. As such, if the camera or a system connected thereto detects a player or individual in the location, the camera may begin automatically recording. In one example, detection of athletes and other individuals may be based on shoes having an RFID tag. Upon detection of the RFID tag, a video camera may be automatically triggered to begin recording the event or athletic activity session. These cameras may be stationary or moveable cameras located at a public, semi-private or private athletic facility (e.g., gym, field, pool, courts, etc.). The location-specific camera data may then be combined with data collected by a user's personal recording device (e.g., a mobile phone with a camera or handheld video camera) during compilation of an athletic activity session file. In some arrangements, the data from different sources may automatically be synchronized upon uploading to a server or other monitoring system.

Data Visualization and Modification

Figure 11:
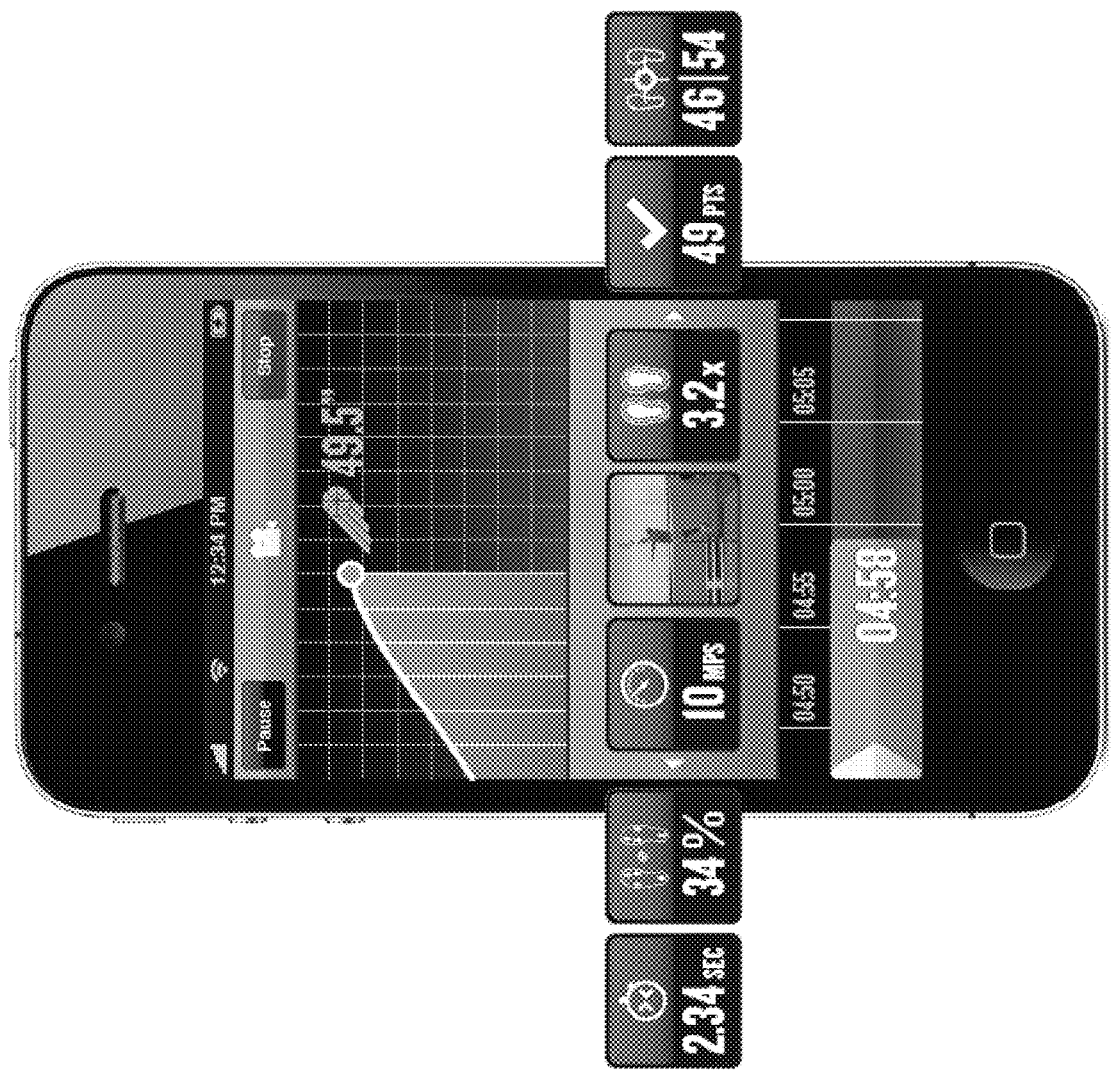
FIG. 11 illustrates another example interface displaying user activity metrics according to one or more aspects described herein.

FIG. 11 illustrates an interface displaying a recorded activity session and expanded metric toolbar and display of a vertical jump metric in the primary visualization area. As discussed, by selecting one of the directional arrows, the metric toolbar may be scrolled to display other metric widgets. An arrow might not be displayed if no additional metric widgets exist in that direction. Scrolling may also be performed using gestures such as swiping to the left or to the right.

Upon selecting a new metric, such as vertical jump, to view in the primary visualization area, the previous metric or interface displayed in the primary visualization area may be reduced to widget or toolbar size and placed in the toolbar. For example, the video that was previous displayed in the primary visualization area may be reduced to a smaller size suitable for the metric widget toolbar and displayed therein. When enlarged or placed into the primary visualization area, the metric widget may display additional or more extensive information as compared to what is displayed in the metric widget toolbar. For example, in the primary visualization area, the vertical jump metric widget displays a current vertical jump value as well as historical vertical jump values for the activity session in a graph. This may allow the user to better understand his or her progress and improvement (if any) during the activity session. The current value of 49.5 inches (i.e., the value associated with the selected or current time in the timeline) may be displayed as well. Each of the widget metrics may include animations when new metric data is received and as time progresses. For example, with respect to vertical jump, the line may extend slightly to the next vertical jump value detected once the timeline advances to a subsequent point in time. In another example, the line may retract if the user decides to rewind and go back to a previous point in time. Metric widgets may display live and animated information in the primary visualization area as well as in the metric toolbar.

Figure 12:
FIG. 12 illustrates an example landscape display of a user's activity metrics with overlaid metric information according to one or more aspects described herein.

FIG. 12 illustrates another example interface displaying video of an athletic activity session along with a timeline representing the duration of the session. In this example interface, the video may be displayed in landscape format and a metric widget toolbar may be hidden or otherwise not displayed to conserve space. However, the timeline may still be displayed to allow a user to jump back and forth in time or to fast forward or rewind as desired. The timeline and/or the metric widget toolbar may be revealed and/or hidden at will based on user interactions with the device on which the interface is displayed. For example, a user may make a first gesture along a touch screen interface to reveal the metric widget toolbar and a second gesture to hide the toolbar. Hiding and displaying of the timeline may be similarly controlled.

According to one aspect, various metrics may be displayed as overlays on the primary visualization area. That is, the information being displayed in the primary visualization area may still be visible beneath the metric overlays. The user may select the desired metrics to be overlain on the primary visualization area. Overlaid metrics may also be hidden if desired. The user may also customize the number of metrics that are displayed over the primary visualization area as well as their appearance including color, font, size, representative symbol, unit of measure and the like. In one example, the best or optimum metric may be called out using highlighting, color, flashing, patterns and the like. In other arrangements, the overlaid information may be displayed with information about personal bests to show how far a user is from matching or exceeding their personal best. Additionally or alternatively, comments, words of encouragement and the like may also be displayed as overlays, in the toolbar or in an information bar of the interface.

Figure 16A:
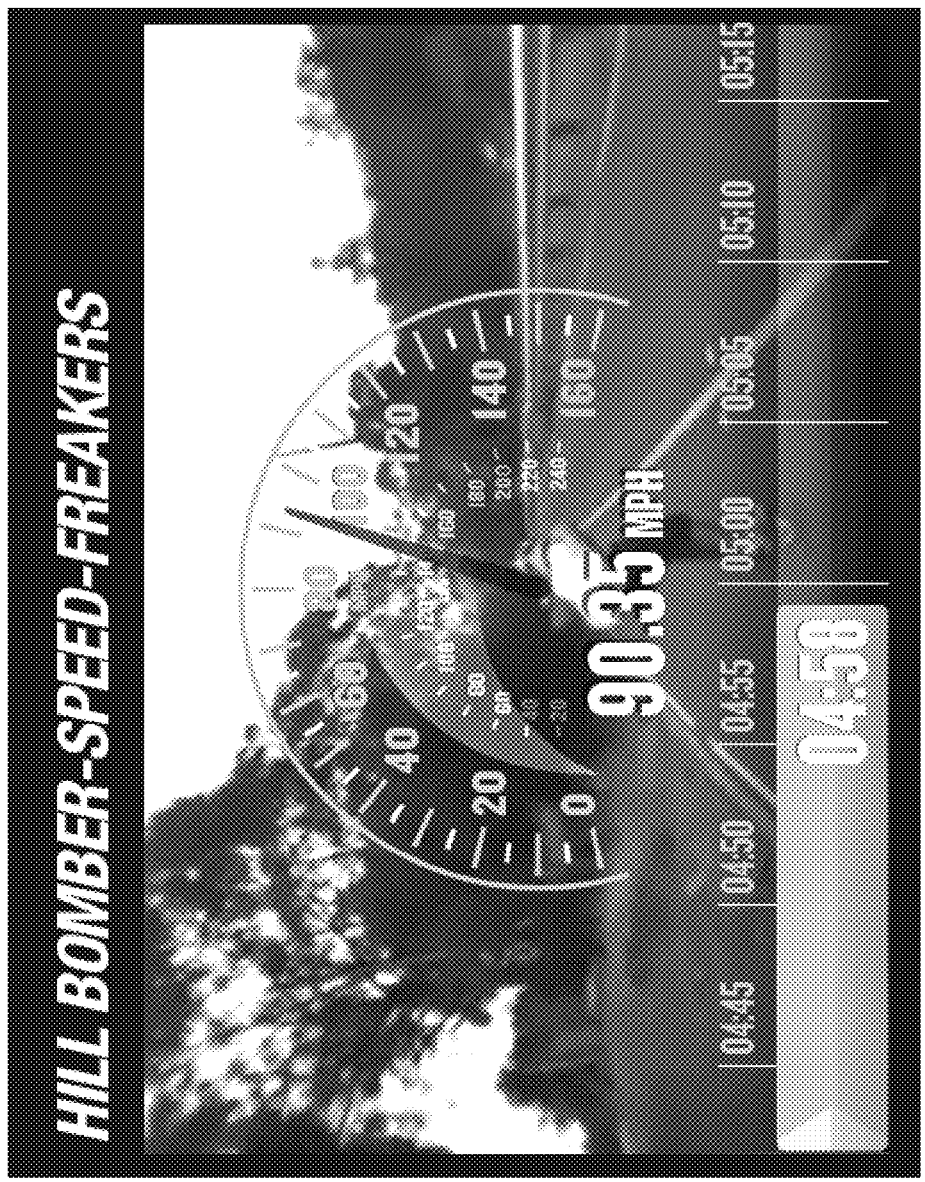
FIGS. 16A and 16B illustrate example display overlays for conveying activity metrics according to one or more aspects described herein.
Figure 16B:

FIGS. 16A and 16B illustrate example metric overlays. In FIG. 16A, for example, a user's speed is displayed as a semi-transparent odometer overlaid on top of the user's skateboard activity session video.

In FIG. 16B, the user's impact is displayed as an arrow with an indicator of the impact magnitude over a video of the user jumping.

Overlaid metric information may include videos of other portions of the activity session or other activity sessions (e.g., of the present user or of other users). In one example, the user may overlay video from an activity session of a pro athlete to compare performance.

FIG. 17A illustrates an example side by side video comparison between a user and a celebrity athlete or other user. In particular, the comparison illustrates the difference in air or flight time. The videos may be cued to a similar point in time such as when a user leaves the ground to perform a dunk. This time may be identified based on indicators stored in association with each respective video or based on pre-processed or on-the-fly image analysis. Comparison between two users may include synchronizing the timelines of athletic activity performances of the two users. For example, if two users performed a 20 minutes run, the system may synchronize the two timelines temporally or otherwise to compare the paces at different points during the 20 minute run. Synchronization may include aligning the two timelines to match up the elapsed time. The system may further allow the users to view video, hear audio or view animated data as the timeline is traversed.

Figure 17B:
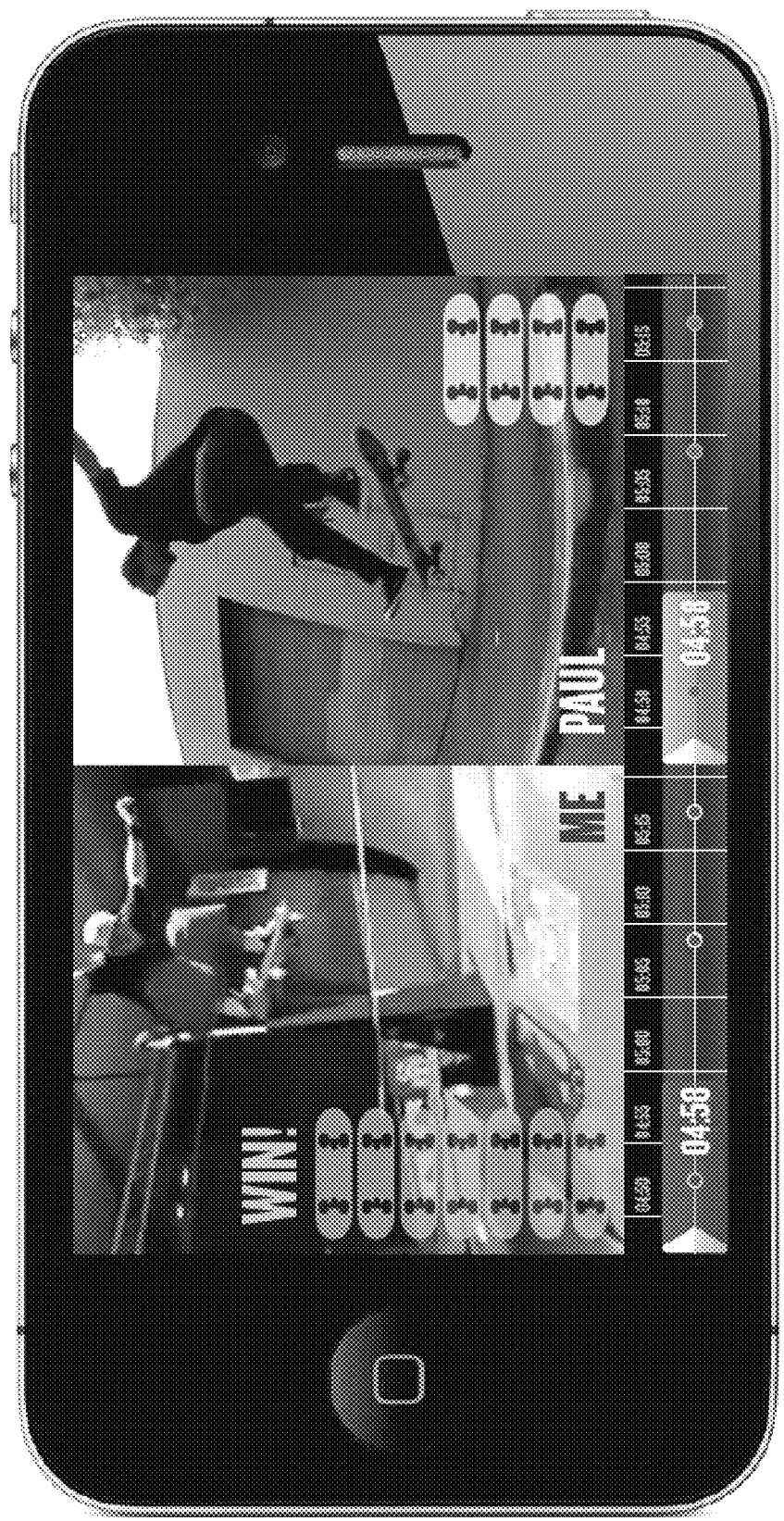

FIG. 17B illustrates another example video comparison between a skateboarder user and a pro or competitor skateboarder. In the illustrated example, the comparison may display a metric using a representative symbol such as a skateboard. That is, the skateboard may represent a number of ollies performed.

Figure 17D:
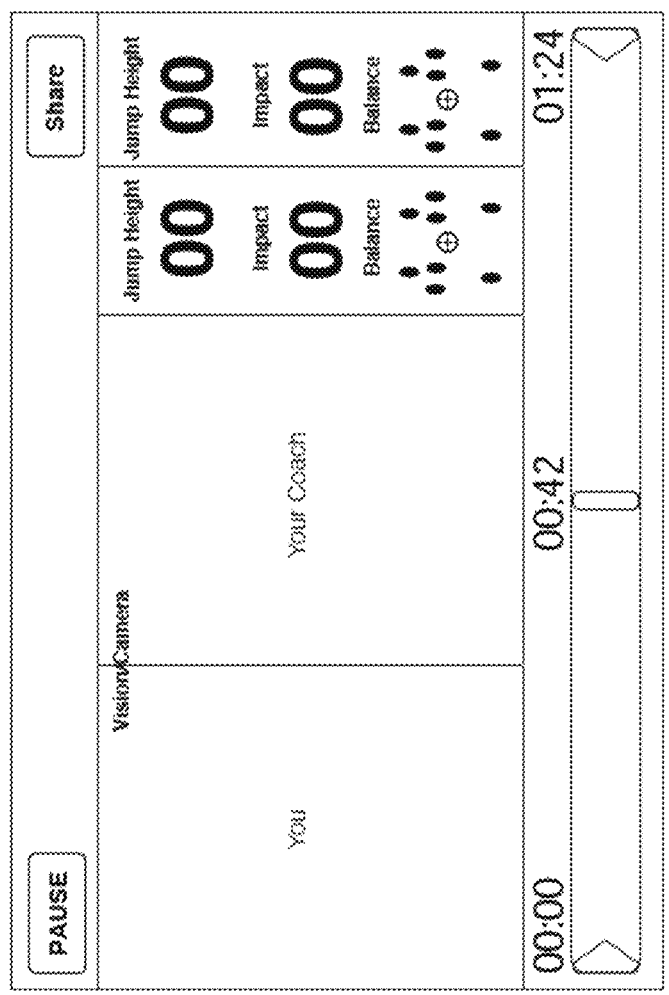
Figure 17C:
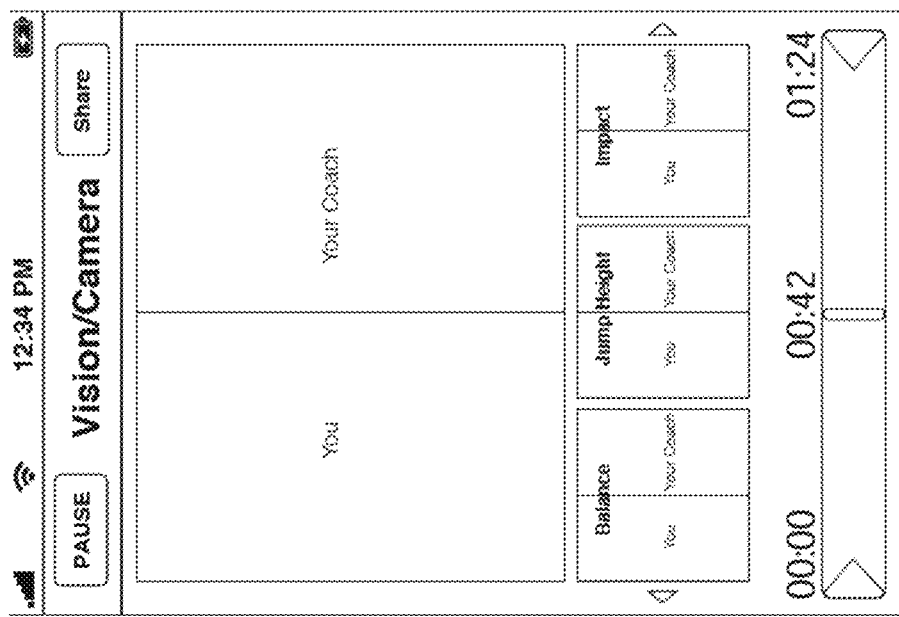

FIGS. 17C and 17D illustrate wireframe representations of interfaces that may also be used to compare the performance of different users. For example, FIG. 17C illustrates a comparison of the performance of an athlete with the performance of the athlete's coach. The widget applications displayed in the toolbar may be displayed with a both the athlete's performance metric as well as the coach's performance metric in a split screen style. Similarly, video of the athlete and the coach may be displayed as split screen in the primary visualization area.

FIG. 17D illustrates a comparison interface that may be displayed in landscape format. Instead of displaying a widget toolbar, the interface may display X number of metrics. In this example, the number of metrics may be 4 (video, jump height, impact and balance). The video may be displayed in split screen and two columns may be displayed adjacent the video, one representing the metrics of the athlete and the other column displaying the metrics of the coach. The interface configurations of FIGS. 17C and 17D may be used to compare the athletic performance of any number of athletes (e.g., 2, 3, 5, 10, etc.) and the athletes may have any type of relationship (e.g., friends, competitions, coach-player/trainee, etc.).

Video overlays may automatically be triggered based on detection of various events such as releasing a pitch, executing a slam dunk and/or throwing a football. For example, video of a professional pitcher's pitch may be overlaid on top of a video of a user's pitch to facilitate visual comparison between the two. Additionally or alternatively, metrics for the overlaid video and the user's video may be displayed in conjunction with one another for comparison purposes. The two sets of metrics may be visually distinguished from one another. For example, a first set of metrics may be displayed in one color while the other set of metrics may be displayed in a second color. Font size, fonts, font style (e.g. bold, italic, underline), pattern, and the like may also be used for visual distinction. Videos that are displayed simultaneously (e.g., one overlaying the other) might also be scaled such that the subject of the videos are displayed in sufficient large size. For example, if a user is far in the distance in one video, the video may zoom in or enlarge the portion containing the user.

Additionally or alternatively, the user may customize appearance of the timeline and/or metric overlays using thresholds. For example, upon a timeline reaching 75% completion, the timeline may change in appearance (e.g., color, pattern, shape, size, etc.). In another example, the metric information may change in color or other appearance if the metric goes above or below a defined threshold (e.g., red colored lettering when pace goes below a 6 minute mile).

Figure 13:
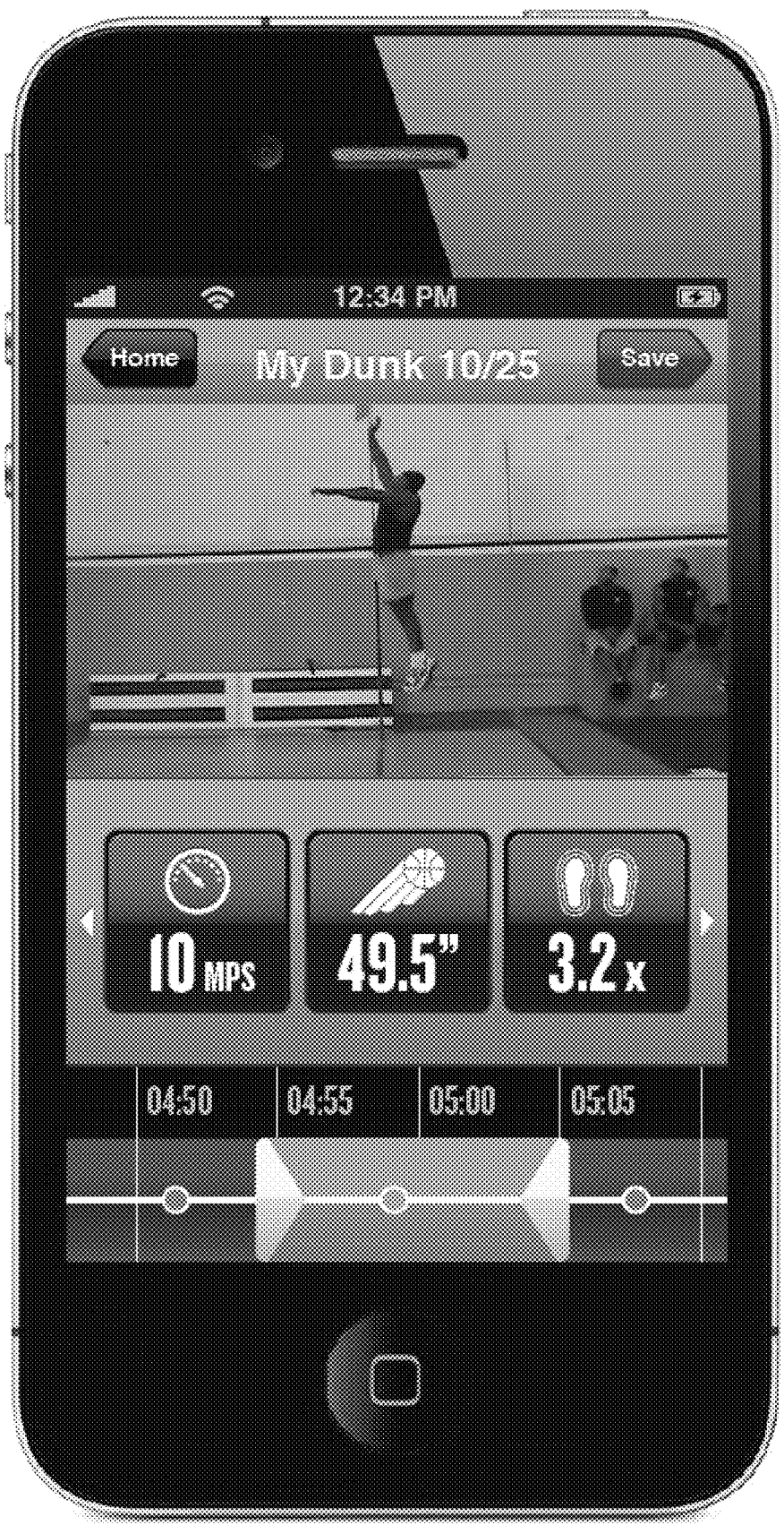
FIG. 13 illustrates an example interface in which a user may crop a recorded activity session according to one or more aspects described herein.

FIG. 13 illustrates an interface through which a user may crop or select a portion (e.g., less than all) of the overall duration of the recorded activity session. The selected portion may thus have a time period or duration representative of a sub-time period of the overall duration. The user may then separate out the selected portion for further processing, analysis and/or sharing with others. For example, the cropped portion or the entire recorded session along with the metrics associated therewith may be uploaded to a social networking site, saved to an athletic performance monitoring service site or emailed to friends. In one or more arrangements, if average metrics are provided for the entirety of the activity session, the user's selection or cropping of a portion of the activity session may automatically cause the system to modify the average to reflect an average of just the selected or cropped portion. A save option allows the user the save the selected portion. Additionally or alternatively, the monitoring system may automatically save the cropped portion and the remaining portion as separate files or data items. This may prevent a user from accidentally deleting a portion of the activity session.

A user may further be allowed to select a particular metric value and the system may automatically identify and display a portion of content file (e.g., a video or audio file) to a time of the athletic activity session at which the particular metric value was recorded. Alternatively or additionally, the user may select a portion (e.g., a range or a specific time) of the content file and one or more metric values specific to the select portion may be displayed.

The timeline may further include one or more indicators identifying certain events of the user's activity session. For example, times corresponding to the user's highest or best values with respect to one or more metrics may be marked within the timeline. Thus, if a user achieves his or her highest vertical jump at time 2:03, an indicator may be placed at the 2:03 point within the timeline. Indicators may be color coded and/or labeled to provide some information about what is being marked. According to one aspect, if a user selects a portion of the timeline (rather than the entire timeline), the indicators may be modified to reflect and identify the best (e.g., highest or lowest) metric values measured for the user during the selected portion. For example, the system may automatically determine the best metric values for the selected portion of the activity session. Alternatively, the indicators might not be modified so that the user is aware of his or her metrics throughout the entire activity session. According to yet another alternative, further indicators may be added in addition to the already existing indicators. For example, the additional indicators may identify the best times and/or other metrics for the selected portion of the activity session. The user may further name the cropped portion upon saving. The saved name may be displayed in the title bar. Indicators may also be used to identify other events that do not correspond to a best metric. For example, the indicators may identify substantial changes in pace (e.g., going from a 12 minute mile pace to a 7 minute mile pace within a predefined amount of time like 1 minute), slam dunks, tennis aces, dancing moves, tackles, football passes of greater than 20 yards and the like. Indicators may also specify the lowest metrics or points in the activity session where a user may need improvement (e.g., coaching or improvement tips).

Selection or cropping of a portion of the video may be performed by a user sliding his or her finger along the timeline (e.g., using a touch screen interface) to desired start and end times for a desired portion. With the above described indicators, the user may more easily select a portion or multiple portions of the video of his or her highlights (e.g., best performance times). Alternatively, the user may use a cursor or time entry fields to specify the start and end times. In one or more arrangements, the user may ask the monitoring system to automatically select the portion. For example, the user may request that the monitoring system crop the video such that only a portion containing a time or period of time at which a user's best dunk (e.g., most air-time, highest rating by the user and/or other users) or highest value of a particular metric was achieved is retained. In a particular example, the system may automatically retain the event along with a predefined amount of time (e.g., 2 minutes, 1 minute, 30 seconds, 15 seconds) around the event. Metric data might only be retained for the remaining portion of the activity session. Additionally, new averages may be calculated for the retained portion upon cropping the non-selected portions. Metric data for a non-retained portion of the activity session, on the other hand, may be discarded or saved to a different file (e.g., a file of the cropped portion). Alternatively or additionally, an average for the non-retained portion may also be automatically generated for comparison purposes in one or more examples.

The cropped video may also be automatically stored as a discrete content file that may be rendered (e.g., viewed, audibly played, visually played) independently of other content files or sets of athletic data. The discrete content file may also correspond to an audio file (e.g., with or without video), or an application file that animates the sequence of recorded athletic data. A user may also select multiple portions of the recorded athletic activity session and each of the selected portions may be stored as a discrete content file. Thus, a user may create multiple content files at one time by selecting multiple portions of the activity session.

Figure 14:
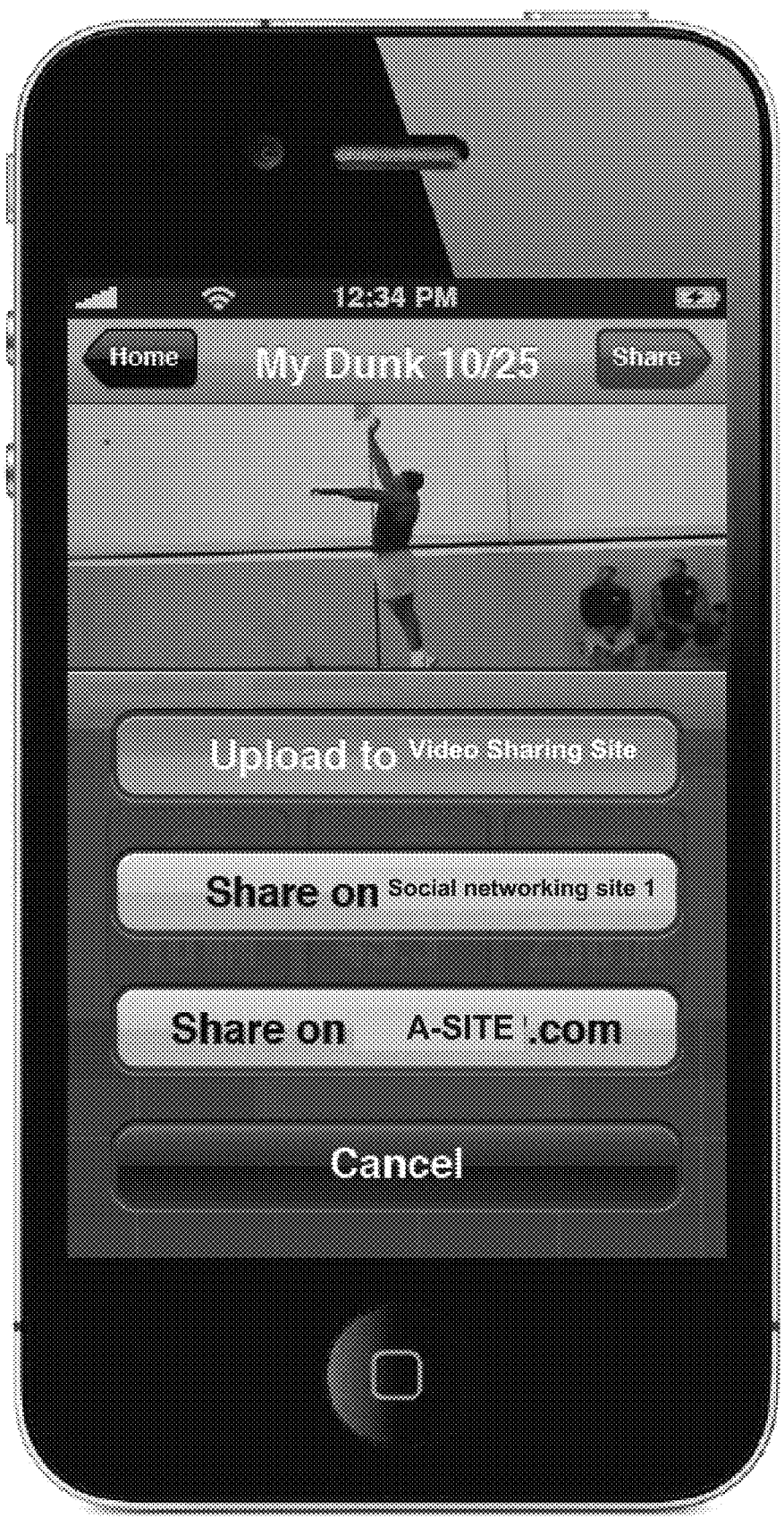
FIG. 14 illustrates an example interface through which a recorded activity session may be shared according to one or more aspects described herein.

FIG. 14 illustrates a video/metric sharing interface that may be displayed after a user has selected a save option (e.g., as shown in FIG. 13). The sharing interface may include one or more predefined sharing options (e.g., for YOUTUBE, FACEBOOK and the like). The interface may further allow a user to customize or define their own sharing sites (e.g., by entering a website or network address).

Figure 15:
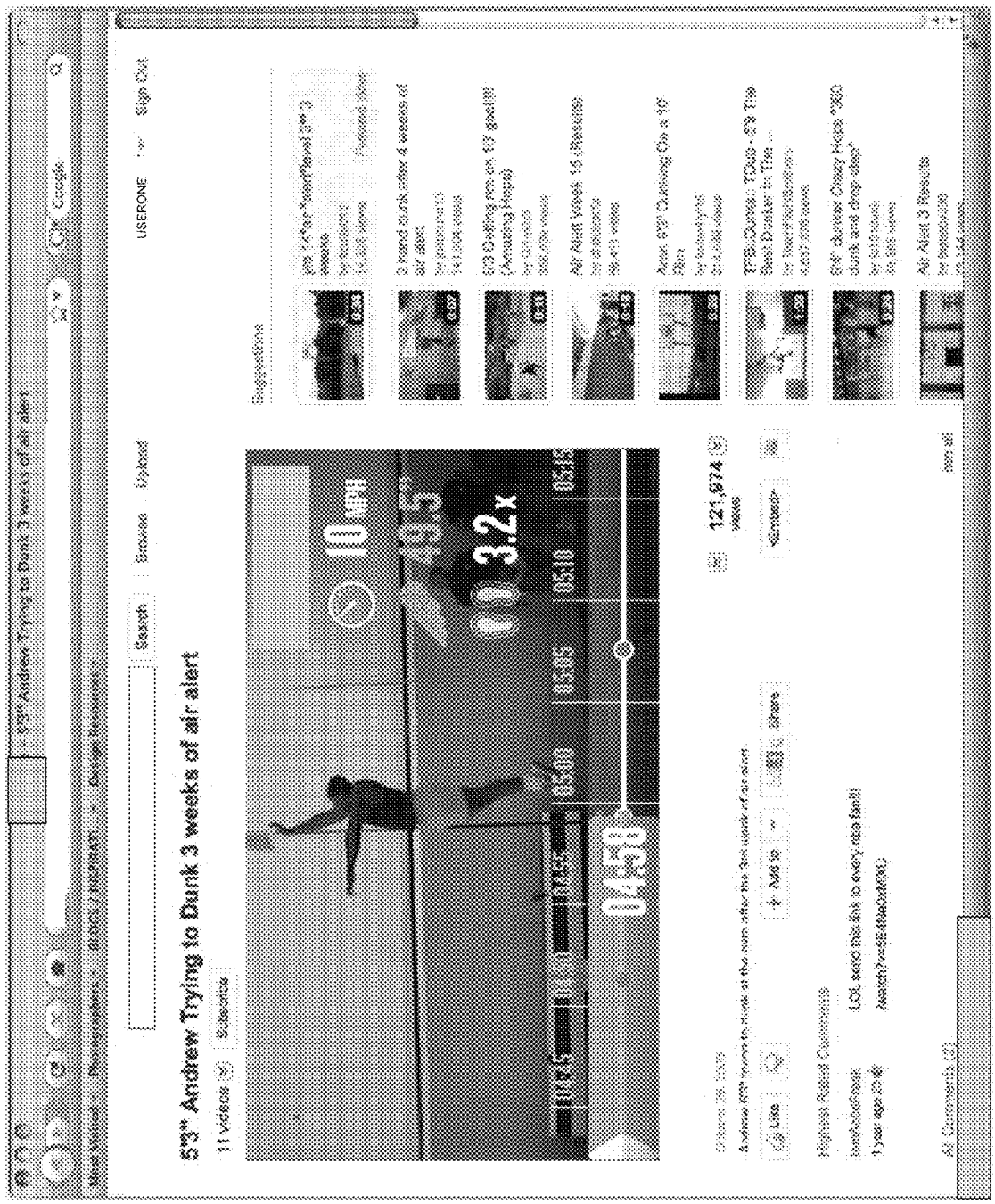
FIG. 15 illustrates an example community website through which recorded activity metrics may be shared according to one or more aspects described herein.

FIG. 15 illustrates a community website displaying a shared video that includes metrics associated with the user showcased in the shared video. On the community website, a variety of individuals may submit comments about the video and/or the user's athletic performance. In one example, coaches may submit comments to help the user improve or to further encourage the user. Comments may be associated with specific times similarly to metric information. Accordingly, comments may only be triggered or displayed upon reaching a particular time of the video. The user may specify permissions for who may comment on the video and/or video the video. For example, the user may indicate that only a certain group of people, specific individuals, or individuals satisfying user-defined criteria (e.g., age, location, affiliation, etc.) are allowed to submit comments or to rate the video/metrics. The user may also specify separate permissions for the video and the metrics. Thus, some users may be able to view both the video and the metrics while other users might only be privy to the video or only the metrics.

Other videos may be suggested for viewing to individuals that are accessing the present video. The other videos may be selected based on type of athletic activity, a subject's age, gender or location, a subject's school or gym, similarity between the subject's performance the performance of the subjects in the other videos and/or other criteria.

Figure 18A:
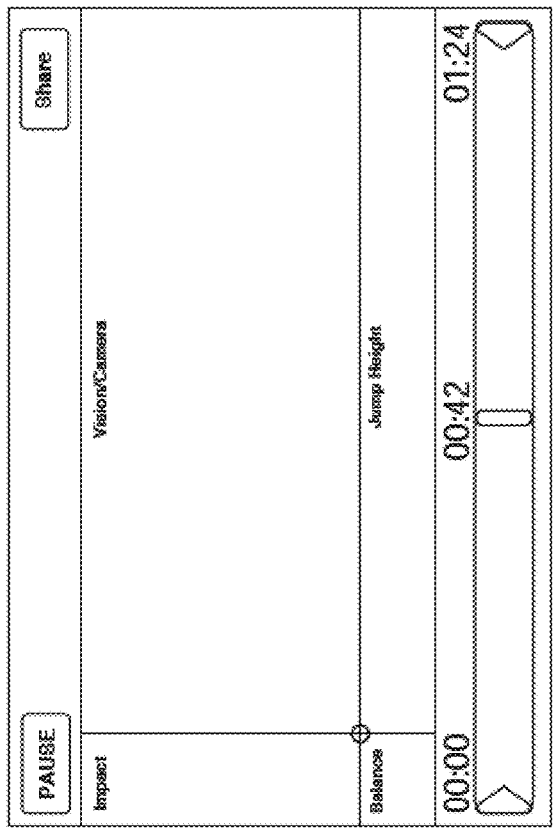
FIGS. 18A and 18B illustrate example interfaces that may be adjusted using an intersection point between display regions according to one or more aspects described herein.
Figure 18B:
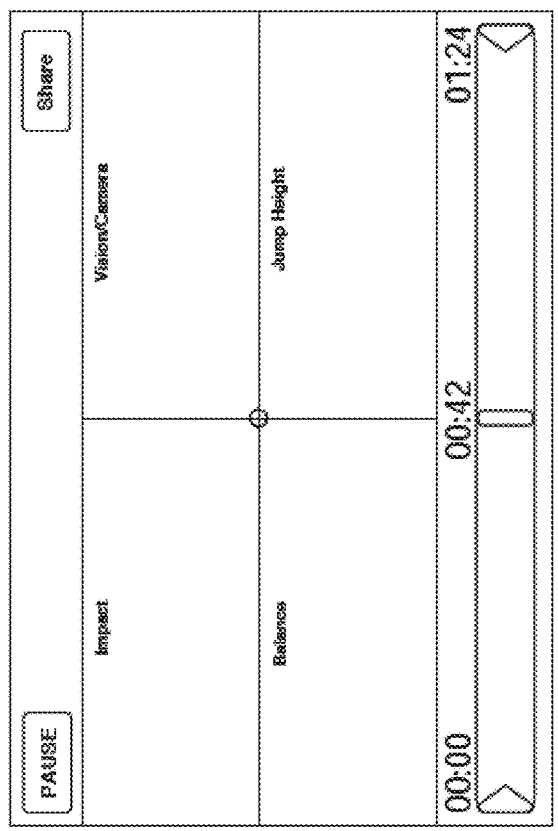

FIGS. 18A and 18B illustrate a series of interfaces in which metrics may be displayed in different regions of a performance visualization area. The user may then be able to adjust the size of the regions by moving an intersection between the different regions. The size of each region may then automatically adjust according to the location of the intersection. For example, in FIG. 18A, the intersection is displayed in the middle of the visualization area, thereby providing each metric with equal display space. The user may then decide to move the intersection (e.g., by selecting and dragging the intersection using a touch screen) to another location as shown in FIG. 18B. Upon the user moving the intersection to the location shown in FIG. 18B, the sizes of the various regions may automatically change to compensate for the new intersection. For example, the width of the impact and balance metric display regions may decrease while the width of the vision/video and jump height metric display regions may be increased. Additionally, the heights of the vision/video metric and impact metric regions may increase while the height of the balance and jump height regions may decrease.

In one or more configurations, a user may be allowed to edit parameters or aspects of a recorded activity session before all recorded metrics are combined into a single activity session file or content item. Additionally, cropping may be performed before the session is compiled into the single file or content item. FIG. 19, for example, illustrates a process whereby a user may select or deselect metrics that are to be combined and stored into a file corresponding to an athletic activity session. Accordingly, even if the various widget applications recorded 8 different metrics, the user may select only 5 of the 8 metrics to be compiled into the activity session file. Alternatively or additionally, the user may define the placement of the various metrics and widget applications in a display area so that the system may assemble the video and other data in a desired manner Still further, a user may add comments, audio (e.g., a soundtrack, narration, sound effects, etc.), interactive buttons (e.g., to send the athlete an email, download the video and the like) and the like.

Video, audio or other athletic performance content data may further be associated with location information. For example, location may be used as a metric as noted herein. Additionally, information about a particular location may be displayed, stored and/or associated with the athletic performance or portion thereof in a granular manner For example, location information for a user's location at each minimum time unit (e.g., second, 1 minute, 5 minutes, 30 minutes, etc.) may be retrieved and stored. Thus, if a user is in a park at minute 1 and later runs to a bridge at minute 8, information about the park may be associated with the athletic performance at minute 1 and information about the bridge may be associated with the athletic performance at minute 8. The location description information may be descriptive of a type of location, history of the location, events occurring at the location and the like. The location description information may then be displayed while the user views a progression of the athletic performance data (e.g., video or audio or animated data).

CONCLUSION

While the invention has been described with respect to specific examples including presently preferred modes of carrying out the invention, those skilled in the art will appreciate that there are numerous variations and permutations of the above described systems and methods. For example, various aspects of the invention may be used in different combinations and various different subcombinations of aspects of the invention may be used together in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly as set forth in the appended claims.

We claim:

1. An athletic parameter measurement device comprising:
a display;
a processor; and
at least one measurement sensor,
wherein the athletic parameter measurement device is configured to:
   detect athletic data of the athlete during an athletic activity session;
   receive, by the processor, video data of the athlete during the athletic activity session;
   calculate, by the processor, at least one metric of the athlete using the detected athletic data and the received video data, wherein the at least one metric includes a location metric of the athlete; and
   trigger a display, by a detection of an event in the video data and by the processor on the display, during performance of the athletic activity session, a representation of the at least one metric, wherein the at least one metric is an overlaid graphic that is displayed during playback of the video data.

2. The athletic parameter measurement device of claim 1, wherein the representation of the at least one metric is displayed in real time.

3. The athletic parameter measurement device of claim 1, wherein the at least one measurement sensor includes a GPS sensor.

4. The athletic parameter measurement device of claim 1, wherein the at least one metric further includes a speed of a user.

5. The athletic parameter measurement device of claim 1, wherein the athletic parameter device is further configured to:
   associate an identification of the athlete with the athletic parameter measurement device; and
   transmit the at least one metric and the identification to a computing device remote from the athletic parameter measurement device.

6. The athletic parameter measurement device of claim 5, wherein the athletic parameter measurement device is further configured to transmit the at least one metric and the identification to the computing device via 2400 and 2483.5 MHz frequency signals.

7. The athletic parameter measurement device of claim 6, wherein the athletic parameter measurement device is further configured to transmit the at least one metric and the identification to the computing device in real-time.

8. The athletic parameter measurement device of claim 1, wherein the overlaid graphic is animated during playback of the video data.

9. A method comprising:
   detecting, by at least one sensor, athletic data of the athlete during an athletic activity session while the sensor is worn by the athlete;
   receiving, by a processor of an athletic parameter measurement device, video data of the athlete during the athletic activity session;
   calculating, by the processor, at least one metric of the athlete using the detected athletic data; and
   trigger a display, by a detection of an event in the video data and by the processor on the display, during performance of the athletic activity session, a representation of the at least one metric, wherein the at least one metric is an overlaid graphic that is displayed during playback of the video data.

10. The method of claim 9, wherein the sensor includes a GPS sensor and the at least one metric includes a location of the athlete.

11. The method of claim 9, wherein the sensor includes an accelerometer and the at least one metric includes a speed of the athlete.

12. The method of claim 9, wherein the representation of the at least one metric is displayed in real time.

13. The method of claim 9, further comprising:
associating an identification of the athlete with the athletic parameter measurement device; and
transmitting the at least one metric and the identification to a computing device remote from the athletic parameter measurement device.

14. The method of claim 13, wherein the athletic parameter measurement device is further configured to transmit the at least one metric and the identification to the computing device in real-time.

15. The method of claim 9, wherein the overlaid graphic is animated during playback of the video data.

16. A method comprising:
detecting, by at least one athletic parameter sensor, athletic data of the athlete during an athletic activity session;
receiving, by a processor of an athletic parameter measurement device, video data of the athlete during the athletic activity session;
calculating, by the processor, at least one metric of the athlete using the detected athletic data and the received video data, wherein the at least one metric includes a location metric of the athlete; and
trigger a display, by a detection of an event in the video data and by the processor on the display, during performance of the athletic activity session, a representation of the at least one metric, wherein the at least one metric is an overlaid graphic that is displayed during playback of the video data.

17. The method of claim 16, wherein the athletic parameter sensor includes a GPS sensor.

18. The method of claim 16, wherein the athletic parameter sensor includes an accelerometer.

19. The method of claim 16, wherein the representation of the at least one metric is displayed in real time.

20. The method of claim 16, wherein the overlaid graphic is animated during playback of the video data.

* * * * *

UNITED STATES PATENT AND TRADEMARK OFFICE
CERTIFICATE OF CORRECTION

| | |
|---|---|
| PATENT NO. | : 11,600,371 B2 |
| APPLICATION NO. | : 16/853937 |
| DATED | : March 7, 2023 |
| INVENTOR(S) | : Meschter et al. |

It is certified that error appears in the above-identified patent and that said Letters Patent is hereby corrected as shown below:

On the Title Page

Column 1, Item (63) Related U.S. Application Data, Line 1:
Delete "(60)" and insert --(63)-- therefor Signed and Sealed this
Eighth Day of October, 2024

Katherine Kelly Vidal
*Director of the United States Patent and Trademark Office*